US012582616B2

(12) United States Patent
Kauvar et al.

(10) Patent No.: US 12,582,616 B2
(45) Date of Patent: Mar. 24, 2026

(54) MOLECULAR TARGETS FOR MODULATION OF DISSOCIATIVE AND ASSOCIATIVE STATES

(71) Applicant: The Board of Trustees of the Leland Stanford Junior University, Stanford, CA (US)

(72) Inventors: Isaac V. Kauvar, Atherton, CA (US); Sam Vesuna, Palo Alto, CA (US); Karl A. Deisseroth, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 437 days.

(21) Appl. No.: 18/019,386

(22) PCT Filed: Aug. 9, 2021

(86) PCT No.: PCT/US2021/045249
§ 371 (c)(1),
(2) Date: Feb. 2, 2023

(87) PCT Pub. No.: WO2022/035773
PCT Pub. Date: Feb. 17, 2022

(65) Prior Publication Data
US 2023/0270693 A1 Aug. 31, 2023

Related U.S. Application Data

(60) Provisional application No. 63/063,765, filed on Aug. 10, 2020.

(51) Int. Cl.
| | |
|---|---|
| *A61K 31/135* | (2006.01) |
| *A61K 31/05* | (2006.01) |
| *A61K 31/13* | (2006.01) |
| *A61K 31/167* | (2006.01) |
| *A61K 31/451* | (2006.01) |
| *A61K 31/48* | (2006.01) |
| *A61K 31/485* | (2006.01) |
| *A61K 31/54* | (2006.01) |
| *A61K 31/5513* | (2006.01) |
| *A61K 38/17* | (2006.01) |
| *A61K 41/00* | (2020.01) |
| *A61K 48/00* | (2006.01) |
| *A61N 1/36* | (2006.01) |
| *A61N 5/06* | (2006.01) |
| *A61N 5/067* | (2006.01) |
| *A61P 25/00* | (2006.01) |

(52) U.S. Cl.
CPC ............ *A61K 31/135* (2013.01); *A61K 31/05* (2013.01); *A61K 31/13* (2013.01); *A61K 31/167* (2013.01); *A61K 31/451* (2013.01); *A61K 31/48* (2013.01); *A61K 31/485* (2013.01); *A61K 31/54* (2013.01); *A61K 31/5513* (2013.01); *A61K 38/177* (2013.01); *A61K 41/00* (2013.01); *A61K 48/0041* (2013.01); *A61K 48/005* (2013.01); *A61N 1/3606* (2013.01); *A61N 1/36157* (2013.01); *A61N 1/36171* (2013.01); *A61N 5/062* (2013.01); *A61N 5/067* (2021.08); *A61P 25/00* (2018.01); *A61N 2005/063* (2013.01)

(58) Field of Classification Search
CPC ...... A61K 31/135; A61K 31/05; A61K 31/13; A61K 31/167; A61K 31/451; A61K 31/48; A61K 31/485; A61K 31/54; A61K 31/5513; A61K 38/177; A61K 41/00; A61K 48/0041; A61K 48/005; A61P 25/00; A61N 5/067; A61N 1/3606; A61N 1/36157; A61N 1/36171; A61N 5/062; A61N 2005/063
See application file for complete search history.

(56) References Cited

U.S. PATENT DOCUMENTS

| | | |
|---|---|---|
| 2003/0022813 A1 | 1/2003 | Chaplan et al. |
| 2019/0298740 A1 | 10/2019 | Barbut et al. |
| 2019/0307762 A1 | 10/2019 | Mehra |

FOREIGN PATENT DOCUMENTS

| | | | |
|---|---|---|---|
| WO | WO2006054755 | * | 5/2006 |
| WO | 2011000915 A1 | | 1/2011 |
| WO | 2021007193 A1 | | 1/2021 |

OTHER PUBLICATIONS

Algalaff et al. ( Neurology (2012) 78(1) PO1204).*
Vesuna et al. ( Nature Sep. 16, 2020; 586 (7827):87-94).*
Wang et al. Neurotoxicology 76 (2020) 213-219.*
Liu et al. Chemico-Biological Interactions 319 (2020) 109006.*
Pendekanti et al., (2018) "High-level visual manifestations of epileptic seizures originating from the medial parietal cortex", Epileptic Disord., 20(3):200-203.
Caruana, et al., (2018) "Motor and emotional behaviors elicited by electrical stimulation of the human cingulate cortex" Brain, 141:3035-3051.

(Continued)

*Primary Examiner* — Shirley V Gembeh

(74) *Attorney, Agent, or Firm* — Jenny L. Buchbinder; Bozicevic, Field & Francis LLP

(57) ABSTRACT

Methods of treating a subject for a dissociative disorder and methods of screening agents for the ability to modulate dissociative and associative states in a subject are provided. In particular, agents that alter rhythmic neural activity in the posteromedial cortex can be used to modulate dissociative and associative states in a subject.

4 Claims, 26 Drawing Sheets

(56)                References Cited

OTHER PUBLICATIONS

Anand et al., (2020) "Attenuation of the Neuropsychiatric Effects of Ketamine With Lamotrigine: Support for Hyperglutamatergic Effects of N-methyl-D-aspartate Receptor Antagonists", Arch. Gen. Psychiatry., 57(3):270-276.

Franzini et al., (2007) "Chronic high frequency stimulation of the posteromedial hypothalamus in facial pain syndromes and behaviour disorders", Acta Neurochirurgica Supplements., 97(2):399-406.

Pendekanti et al., (2018) "High-level visual manifestations of epileptic seizures originating from the medial parietal portex", Epileptic Disord., 20(3):200-203.

Vesuna et al., (2020) "Deep posteromedial cortical rhythm in dissociation," Nature., 586(7827):87-94.

* cited by examiner

Hot plate test

Fiber photometry

Widefield Imaging

Figure 3G:
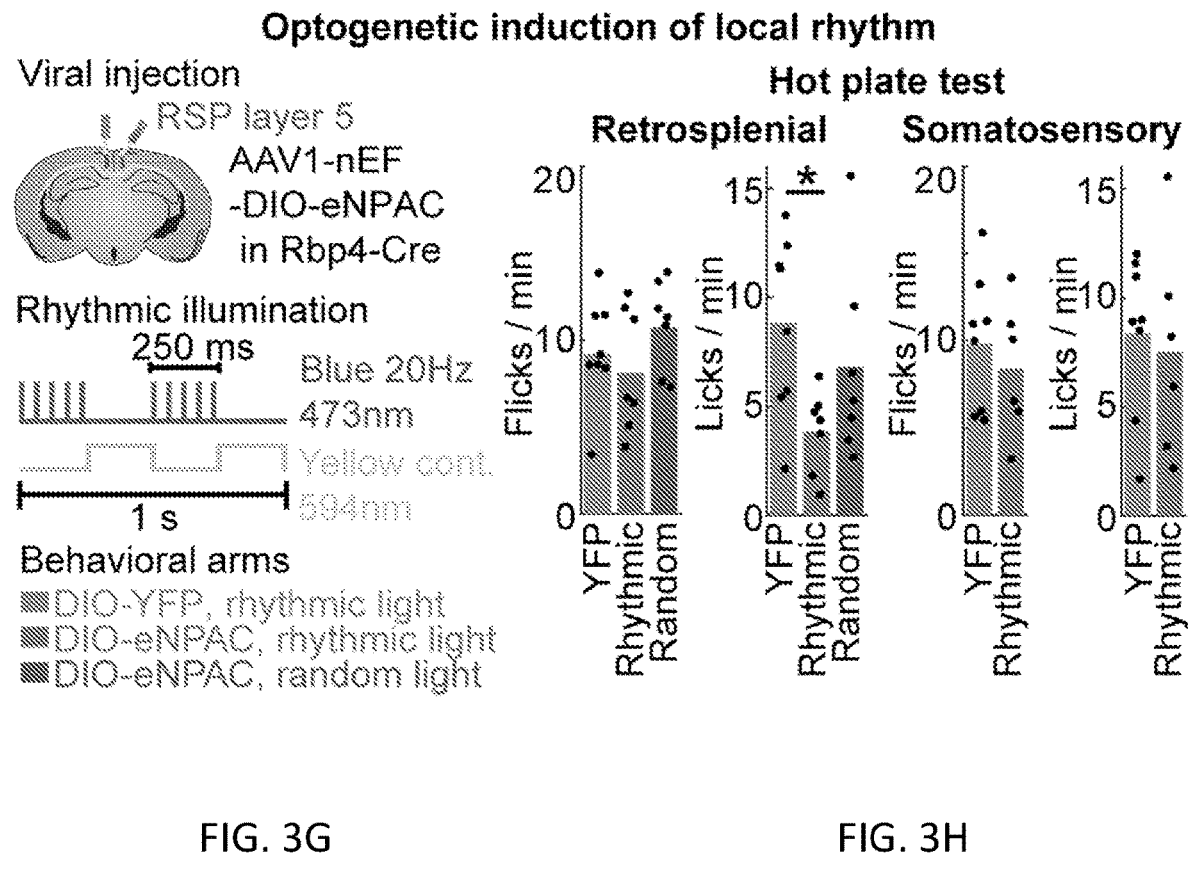

Optogenetic induction of local rhythm

Viral injection

RSP layer 5
AAV1-nEF
-DIO-eNPAC
in Rbp4-Cre

Rhythmic illumination 250 ms

Blue 20Hz
473nm

Yellow cont.
594nm 1 s

Behavioral arms

DIO-YFP, rhythmic light
DIO-eNPAC, rhythmic light
DIO-eNPAC, random light

Hot plate test

Retrospenial          Somatosensory

FIG. 3G                    FIG. 3H

**Potential mechanisms of
induced retrosplenial rhythm**

Through subcortical drive

Dorsal Thalamus

Subiculum

Cortical Dynamics

Subcortical Inputs

Through local channels

Cortical Dynamics

HCN1 or NMDAR
ion channels on
retrosplenial neurons

Monosynaptic inputs to layer 5 retrosplenial

Retrosplenial recording during subcortical inhibition

Photometry in RSP during optogenetic inhibition of dorsal thalamus or subiculum with 50mg/kg ketamine

Human recordings during pre-seizure aura

"I was listening to two parts of my brain speak to each other in a way that a third part of my brain, which I considered to be me, was able to listen."

"what would it feel like if someone else were to come into your head?... What I considered me shrank to this other part of me where the other parts of my brain that were talking, I stopped considering them me."

"...where in this 3D space am I? ... I took a blanket...I threw it over my body, just to see, because I knew that when I don't feel it, I don't consider it me and immediately my legs were no longer a part of me..."

FIG. 5B

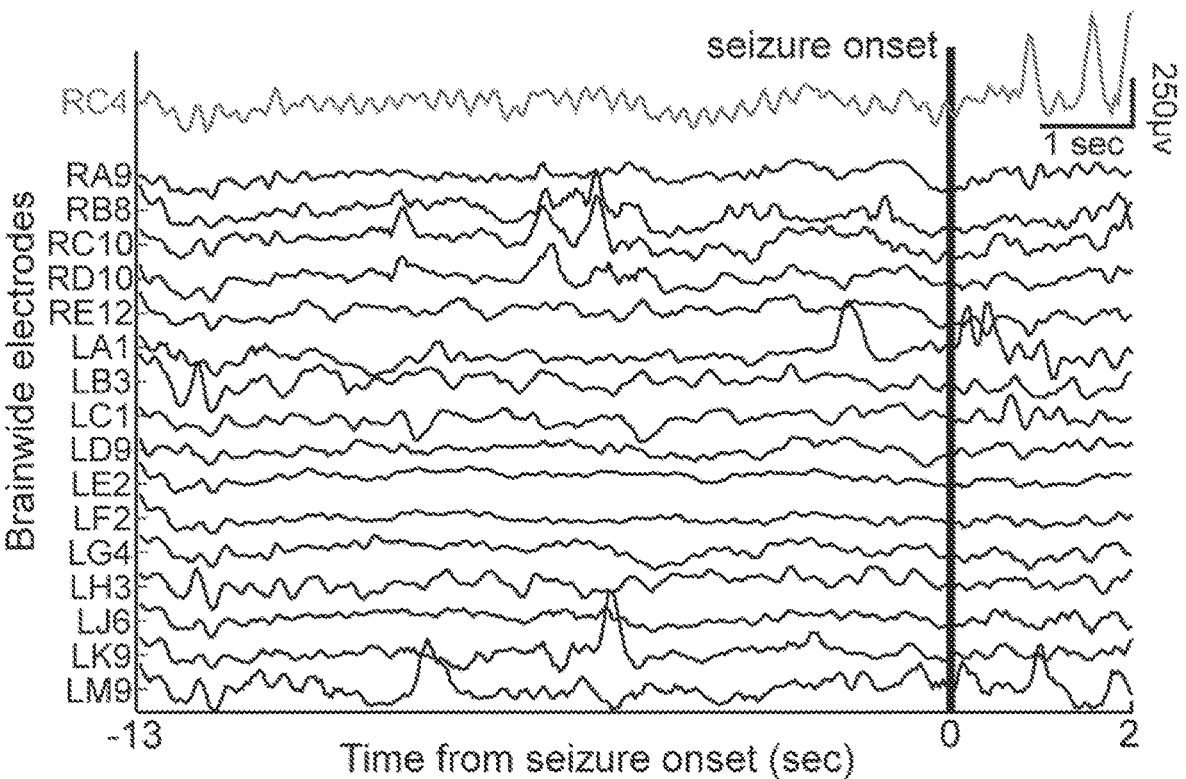

FIG. 5C

Electrical stimulation evoked dissociative experiences

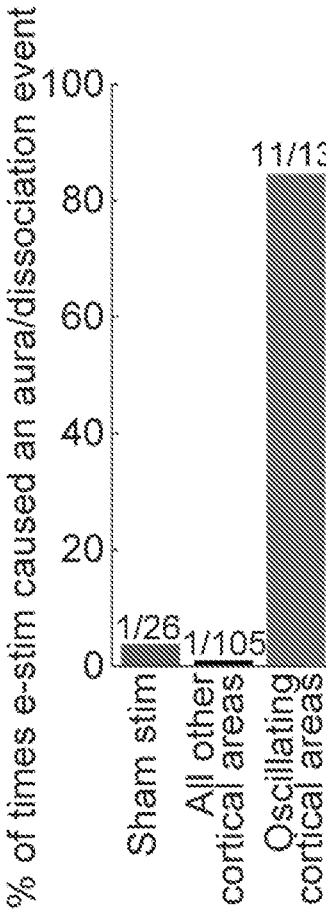

Right Deep PMC

1 "felt similar to the seizure beginning"

2 "felt like an aura"

3 "It's like I'm about to have a seizure"

Posterior
↕
Anterior

Left Deep PMC

4 "this feeling of being disconnected from something... that was a little pleasant"

5 "it's like being weightless in your own mind as a personality"

6 "...maybe the same way a pilot can lose control of a plane. Like they can be forced out of the cockpit or to not control it... but still see what's happening to the whole plane, that's kinda what just happened. I got pulled out of...the pilot's chair, but I could still see all the gauges... You can see the information flowing-- you can't control it, but you can see it."

FIG. 5F

MOLECULAR TARGETS FOR MODULATION OF DISSOCIATIVE AND ASSOCIATIVE STATES

BACKGROUND OF THE INVENTION

Recent advances in large-scale high-speed recording and control of neuronal activity have enabled exploration of natural and causal neural circuit-dynamics spanning the mammalian brain. We considered that these technological advances constitute a newly-emerged opportunity to explore cellular implementation of altered behavioral states that may require a global perspective for understanding. Dissociation represents a paradigmatic example of such a state.

In dissociation (elicited by diverse causes including stress, epilepsy, dissociative drugs, or certain neuropsychiatric disorders), normal integration of cognitive processing is disrupted. A selective uncoupling can be observed, with affective/emotional responses dissociated from sensory percepts, and sense-of-self dissociated from body position/action. The underlying cellular and circuit mechanisms of this fascinating and debilitating state remain unknown, despite substantial basic and clinical significance.

SUMMARY OF THE INVENTION

Methods of treating a subject for a dissociative disorder and methods of screening agents for the ability to modulate dissociative and associative states in a subject are provided. In particular, agents that alter rhythmic neural activity in the posteromedial cortex can be used to modulate dissociative and associative states in a subject.

In one aspect, a composition comprising an inhibitor of a hyperpolarization-activated cyclic nucleotide-gated (HCN) pacemaker channel for use in treatment of a dissociative disorder is provided. Exemplary inhibitors of the HCN pacemaker channel include, without limitation, gabapentin, ivabradine, amiodarone, clonidine, loperamide, bepridil, zatebradine, cilobradine, alinidine, falipamil, ZD7288, CP-339,818, and YS-035. In certain embodiments, the HCN pacemaker channel is a HCN1, HCN2, HCN3, or HCN4 isoform. In certain embodiments, the composition further comprises a pharmaceutically acceptable excipient. In certain embodiments, the dissociative disorder is caused by a drug, a seizure, childhood psychological or physical trauma, abuse, sexual assault, or a dissociation-linked neuropsychiatric disorder. Exemplary dissociation-linked neuropsychiatric disorders include, without limitation, post-traumatic stress disorder (PTSD), borderline personality disorder, and schizophrenia spectrum disorder.

In another aspect, a method of treating a subject for a dissociative disorder is provided, the method comprising administering a therapeutically effective amount of an inhibitor of a hyperpolarization-activated cyclic nucleotide-gated (HCN) pacemaker channel to the subject. In certain embodiments, the inhibitor of the HCN pacemaker channel is gabapentin, ivabradine, amiodarone, clonidine, loperamide, bepridil, zatebradine, cilobradine, alinidine, falipamil, ZD7288, CP-339,818, or YS-035. At least four isoforms of HCN exist, including HCN1, HCN2, HCN3, or HCN4. Thus, in certain embodiments one or more of the isoforms HCN1, HCN2, HCN3, or HCN4, or any combination thereof, are inhibited. Preferably, at least HCN1 is inhibited by the HCN inhibitor. Inhibition may be complete or partial (i.e., all activity, some activity, or most activity is blocked by an inhibitor). For example, an inhibitor may reduce the activity of HCN by 10%, 20%, 30%, 40%, 50%, 60%, 70%, 80%, 90%, 100%, or any amount in between as compared to native or control levels. In certain embodiments, the dissociative disorder is caused by a drug, a seizure, childhood psychological or physical trauma, abuse, sexual assault, or a dissociation-linked neuropsychiatric disorder. Exemplary dissociation-linked neuropsychiatric disorders include, without limitation, post-traumatic stress disorder (PTSD), borderline personality disorder, or schizophrenia spectrum disorder.

The inhibitor of the HCN pacemaker channel can be administered by any medically appropriate mode of administration. In some embodiments, the inhibitor is administered orally, intravenously, intramuscularly, intraperitoneally, intracranially, or locally. In some embodiments, the agent is administered daily or intermittently.

In another aspect, a method of modulating associative or dissociative symptoms in a subject is provided, the method comprising administering an effective amount of an agent that modulates rhythmic neural activity in the posteromedial cortex of the subject.

In certain embodiments, the agent that modulates rhythmic neural activity in the posteromedial cortex is an agent that modulates an HCN pacemaker channel, an agent that modulates N-methyl-D-aspartate receptor (NMDAR), an agent that modulates posteromedial cortical activity, or an agent that modulates monoamine oxidase.

Exemplary agents that modulate an HCN pacemaker channel include, without limitation, gabapentin, lamotrigine, ivabradine, amiodarone, clonidine, and loperamide. In some embodiments, the HCN pacemaker channel is a HCN1, HCN2, HCN3, or HCN4 isoform.

Exemplary agents that modulate posteromedial cortical activity include, without limitation, lidocaine, bupivacaine, propofol, a benzodiazepine, and a barbiturate.

Exemplary agents that modulate an NMDAR include, without limitation, ketamine, dextromethorphan (DXM), phencyclidine (PCP), methoxetamine (MXE), pethidine, levorphanol, methadone, dextropropoxyphene, tramadol, ketobemidone, and etoxadrol.

Exemplary agents that modulate a monoamine oxidase include, without limitation, isocarboxazid, hydracarbazine, phenelzine, tranylcypromine, bifemelane, moclobemide, pirlindole, rasagiline, selegiline, and safinamide.

The agent that modulates rhythmic neural activity in the posteromedial cortex can be administered by any medically appropriate mode of administration. In some embodiments, the inhibitor is administered orally, intravenously, intramuscularly, intraperitoneally, intracranially, or locally. In some embodiments, the agent is administered daily or intermittently.

In certain embodiments, the subject has a dissociative disorder caused by a drug, a seizure, childhood psychological or physical trauma, abuse, or a sexual assault, post-traumatic stress disorder (PTSD), borderline personality disorder, schizophrenia spectrum disorder, In another aspect, a method of screening an agent to determine if the agent induces a dissociative state in a subject is provided, the method comprising: a) administering the agent to the subject; and b) detecting whether the agent induces a rhythmic waveform in the deep posteromedial cortex of the subject.

In another aspect, a method of screening a candidate agent to determine if the candidate agent induces or inhibits a dissociative state in a subject is provided, the method comprising: a) administering the candidate agent to the subject; and b) detecting whether the candidate agent induces or inhibits rhythmic neural activity in the posteromedial cortex of the subject. In some embodiments, the method further comprises administering a dissociative agent (e.g., ketamine or phencyclidine) that induces rhythmic neural activity in the posteromedial cortex; and detecting whether the candidate agent inhibits the rhythmic neural activity induced by the dissociative agent.

Any method known in the art can be used to detect the rhythmic neural activity in the posteromedial cortex of the subject. Exemplary methods for detecting the rhythmic neural activity include, without limitation, electrocorticography (ECoG), electroencephalography (EEG), stereoelectroencephalography (sEEG), magnetoencephalography (MEG), single photon emission computed tomography (SPECT), functional magnetic resonance imaging (fMRI), and positron emission tomography (PET).

BRIEF DESCRIPTION OF THE DRAWINGS

FIG. 1A) Widefield microscope schematic. FIG. 1B) Transparent-skull preparation (left); 488 nm-fluorescence image, Thy1-GCaMP6s animal (right); A=anterior, P=posterior. FIG. 1C) Neocortex atlas for alignment: Motor (MOT), Somatosensory (SS), Parietal (PP), Visual (VIS), Retrosplenial (RSP). FIG. 1D) Video sequence: 410 nm-corrected fluorescence across 1 second in Thy1-GCaMP6s mouse. RSP activation: 0.13s and 0.8s; deactivation 0.54s. FIG. 1E) (top) Fluorescence traces from five regions before (blue) and 10 min after (red) 50 mg/kg ketamine injection. 10s 410-nm corrected data. (bottom) Corresponding power spectral density (PSD) plots, minutes 10-11 post-injection (mean/s.e.m; n=5 mice). FIG. 1F) Frequency-content change after ketamine, n=5 mice. One-way ANOVA, repeated measures, F(4,16)=25.4, p<1e-4. Corrected two-sided paired t-tests (**p<0.01). Hedge's g effect-sizes (3.96,3.90,3.76,3.62). FIG. 1G) 1-3 Hz power in RSP across 55 min, with i.p. injection of 50 mg/kg ketamine 5 min into recording (widefield imaging of GCaMP6s). Mean for n=6 mice: thick trace. FIG. 1H) PCP, MK801, and memantine: mean 1-3 Hz power (n=5 mice per drug), corrected 2-sided paired t-tests (*p<0.05, **p<0.01, ns p>0.05), Hedge's g effect-sizes PCP(4.23,4.57,5.14, 4.87), MK801(1.80,1.79,2.16,1.28,1.56), memantine(1.00, 0.96,0.27,0.82). FIG. 1I) (left) Single-cell activity traces; two-photon microscopy from layer 2/3 or 5 RSP after ketamine injection. (right) Mean 1-3 Hz power before/after ketamine across cells; n=5 mice (two-sided paired t-test, p=0.74 layer 2/3, n=5 mice, Hedge's g effect-size=-0.46; p<0.001 layer 5, n=5 mice, Hedge's g effect-size=3.16). FIG. 1J) tdTomato fluorescence after recombination of TRAP2; Ai14 mice, after 50 mg/kg ketamine injections; dense labeling of layer 5 cells. Dark cells: tdTomato expressing. Scale:1 mm.

FIG. 2A) Spike-train rasters from all simultaneously-recorded single-units from deep RSP in ketamine-injected head-fixed mouse. Below, firing rate of units above (Hz, 10 ms bin). Red boxes: ON-states for bursts (Methods). FIG. 2B) Multi-Neuropixel recording session. Ketamine injected i.p. 20 min into recording via previously-implanted cannula. FIG. 2C) 3D-reconstruction: Neuropixels insertions (all 4 mice, 16 probe-insertions total); brain areas noted by changing colors along each probe. Four Neuropixels implanted/ recorded simultaneously. FIG. 2D) Average firing-rate change per region between 8-12 min before and 8-12 min after ketamine injection. Cells included from all 4 sessions. #units for each region: x label. Mean/s.e.m (corrected two-sided t-test vs. 0). FIG. 2E) Average RSP correlation (mean regional activity) before/after ketamine injection. #units indicated for each region. Mean/s.e.m (corrected two-sided t-test vs. 0). FIG. 2F) Correlation-matrix between cells, grouped by region before/after ketamine injection; 4-Neuropixel recording in mouse. FIG. 2G) Z-scored mean-activity traces; three simultaneously-recorded thalamic nuclei and RSP (green). *p<0.05, p<0.01, *p<0.001

FIGS. 3A-3H. Ketamine- and optogenetically-elicited dissociation-like behavioral phenotype. FIG. 3A) Hot-plate stimulus-detection (reflexive paw-flick) vs. affective/emotional response (protective paw-licking). FIG. 3B) Rate of reflexive paw-flicks/licks in ketamine-injected mice. One-way ANOVA with repeated measures: flick, p=0.38; lick, p=5E-4. Corrected two-sided unpaired t-tests. n=5 mice/ group. For each dose in order, Hedge's g effect-sizes for flick (0.16,0.26,0.77,0.77) and lick (−0.028,0.53,−1.43,−2.19). FIG. 3C) (Left) Fiber photometry traces from RSP: rhythm at 25 mg/kg but not 13 mg/kg. (Right) 10 min after injection, power at each dose across several mice (unpaired-t-test p=0.008, Glass's Δ=3.2). FIG. 3D) Widefield imaging dose-response: mean 1-3 Hz power for 13 and 25 mg/kg doses (n=4 mice, two-sided unpaired t-test, p<0.027). FIG. 3E) Hot-plate test: other drug classes. Each experimental group compared with saline (control) group via corrected Mann-Whitney U-test. For each drug in order, Hedge's g effect-sizes: flick (3.10,−2.97,−2.19,1.14,−2.16), Glass's Δ: lick (−15.2,−2.89,0.093,−0.40,−0.90). FIG. 3F) (Left) Open-field velocity (5 min). Ketamine, LSD and diazepam decreased velocity. Buprenorphine increased velocity. Each experimental group compared with saline (control) via corrected Mann-Whitney U-test. Hedge's g effect-sizes: (−6.14, 1.02,4.98,0.20,−2.34,−4.77). (Right) Traces of body-position with saline or dissociative drugs. Gray line: full 5 min session, black line: 20s tracking (beginning minute-2). FIG. 3G) Viral injections, illumination pattern, behavioral arms. AAV1-nEF-DIO-eNpHR3.0-p2a-ChR2-YFP (eNPAC) injected bilaterally into Rpb4-cre RSP. Illumination: 20 Hz-blue and constant-orange light, alternating every 250 ms. FIG. 3H) Hot-plate: Retrosplenial left to right, paw-flick: YFP/Rhythmic p=0.53, YFP/Rand p=0.48; Rhythmic/Random p=0.43; paw-lick: YFP/Rhythmic p=0.034, YFP/Random p=0.38; Rhythmic/Random p=0.20, corrected two-sided unpaired t-tests, n=8 YFP, 7 Rhythmic, 7 Random mice. Hedge's g effect-sizes for flick (−0.31,0.50,0.79), lick (−1.43,−0.45,0.80). Somatosensory paw-flicks (p=0.50), paw-licks (p=0.71); Hedge's g effect-size for flick:−0.35, lick:−0.19, Two-sided paired t-test, n=8 control, n=6 somatosensory eNPAC mice. *p<0.05; p<0.01, *p<0.001

FIG. 4A) Possible mechanisms underlying RSP rhythm. FIG. 4B) Confocal images: (left to right) RSP, cingulate-cortex, subiculum, and dorsal-thalamus cells, green=GFP, blue=DAPI. Scale 1 mm (right panel). FIG. 4C) (Left) AAVdj-CaMKIIa-eNpHR3.0-YFP injected bilaterally in dorsal-thalamus or subiculum; GCaMP6m expressed in RSP. (Right) 1-3 Hz relative power for pre-, during-, and post-optogenetic-inhibition 2 min epochs beginning 10 min after ketamine injection. Normalized by PSD during the pre-epoch, and then linearly-corrected to account for decrease in oscillation-power across 6 min recording. Thalamus inhibition increased oscillation-power (two-sided paired t-test, YFP p=0.057 n=5 mice, subiculum p=0.91 n=5, thalamus p=0.003 n=7). Hedge's g effect-sizes YFP=0.54, subiculum=0.065, thalamus=2.90. FIG. 4D) Confocal images: immunohistochemistry with antibodies against (top)

GRIN1 or (bottom) HCN1 in wild-type mice. HCN1 image reveals low HCN1+density in superficial RSP. FIG. 4E) (Left) Photometry in RSP. AAVs expressing Cre-recombinase and Cre-dependent GcaMP6 injected for local disruption of NMDA-receptor or HCN1-channel expression. (Middle) Photometry traces. (Right) Reduced ketamine-induced oscillation-power in GRIN1 and HCN1 knockout mice (corrected two-sided paired t-test for within-mouse comparison and corrected two-sided independent t-test for between genotype comparisons, n.s.: p>0.05, *p<0.05, p<0.01, *p<0.001, n=7 mice/group, Hedge's g effect-sizes (WT-pre/WT-post=3.22, GRIN1-pre/GRIN1-post=2.03, HCN1-pre/HCN1-post=1.02, WT-post/HCN1-post=−2.75, WT-post/GRIN1-post=−2.26, HCN1-post/GRIN1-post=1.24, WT-pre/HCN1-pre=0.318, WT-pre/GRIN1-pre=0.322, HCN1-pre/GRIN1-pre=0.09). FIG. 4F) Hot-plate test. Reflexive paw-flicks (corrected Mann-Whitney U-test p>0.1) and affective paw-licks (corrected Mann-Whitney U-test, wild-type-vs-GRIN1, p=0.56; wild-type-vs-HCN1, p<0.001). Hedge's g effect-sizes for flick (0.77, 0.070) and lick (0.40,2.46).

FIGS. 5A-5F. Human posteromedial cortex rhythm and self-reported dissociation. FIG. 5A) Simultaneous sEEG and 3D-electrode locations in patient, 10s before seizure-onset. Contact number (e.g. RC3: R (right-hemisphere) C (electrode-letter) 3 (contact-number) and anatomical-region (e.g. posteromedial). Rhythm observed in PMC in both hemispheres across contacts (magenta) not other regions (black). Contacts on each electrode: dots. FIG. 5B) Comments of patient describing pre-seizure aura experience. Notably, symptoms of dissociation consistently described (APA 2013) can involve reproducible perceptions of depersonalization (feeling of being outside observer of one's body/thoughts) and derealization (feeling of being detached from surroundings). Supplementary note: interview transcript. FIG. 5C) Simultaneously-recorded sEEG traces during pre-seizure epoch; different seizure from (a). One contact per electrode shown in black. Deep PMC contact: magenta. Seizure onset determined by epileptologist: vertical line. FIG. 5D) sEEG traces from deep and superficial PMC during aura (red) or non-seizure (blue) epochs. Mean+/−s.e.m. in (top) right and (bottom) left regions across aura periods. FIG. 5E) 3-4 Hz power during aura (red) or non-seizure/aura period (blue). Mean across channels in each region; aura periods: black dot. FIG. 5F) (Left) Patient's electrode locations (colored dots). Electrodes in deep PMC accentuated with blue (right) and gray (left) indicators. Comments describing experience during electrical stimulation of deep PMC shown. (Right) fraction of time aura reported for each sham or electrical stimulation (≥6 mA).

DETAILED DESCRIPTION

Figure 1A:
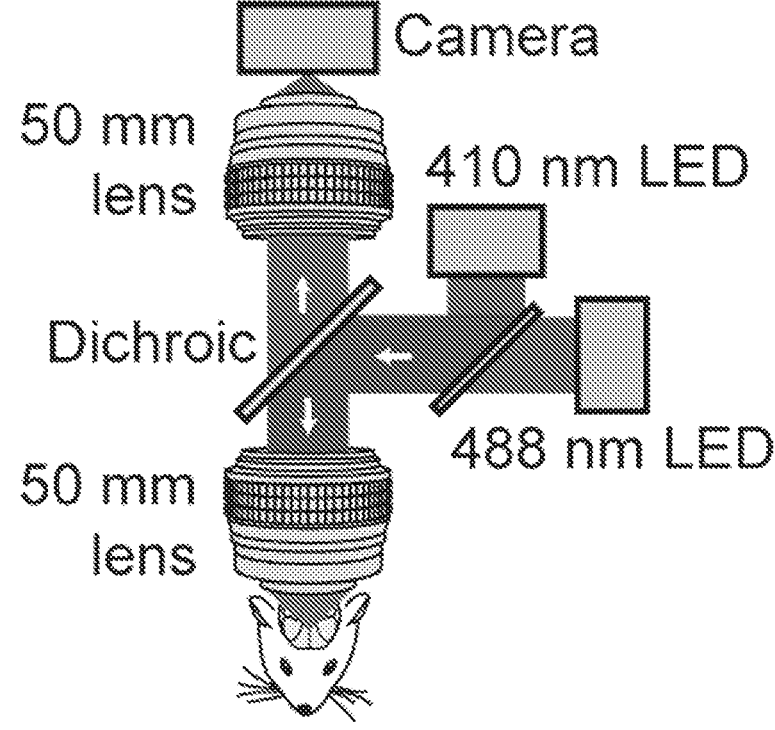
FIGS. 1A-1J. Multiregional widefield imaging of cortical activity reveals ketamine-induced retrosplenial rhythm.
Figure 1B:
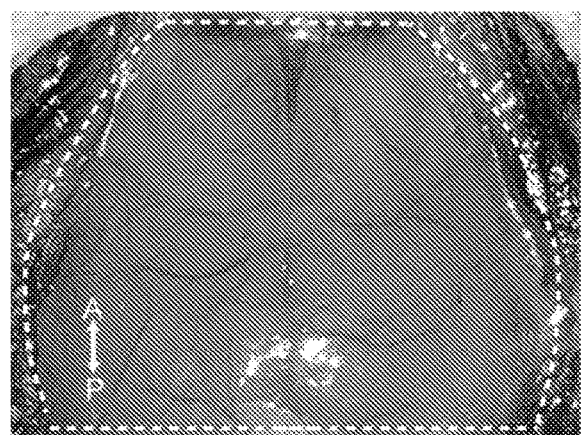
Figure 1B:
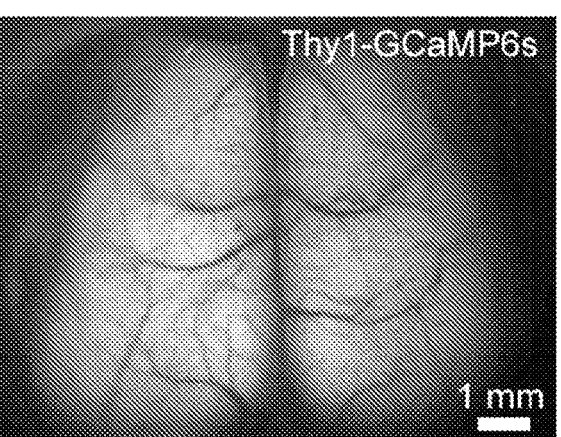
Figure 1C:
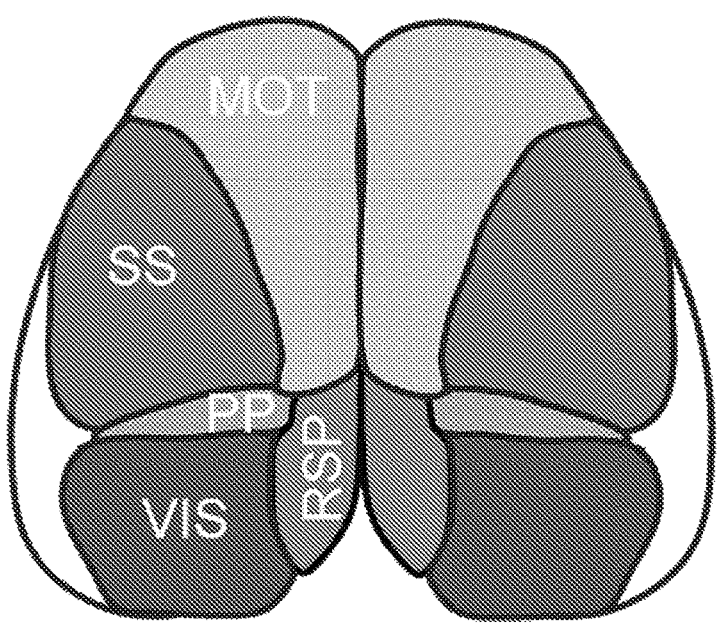

Before the methods of treating a dissociative state in a subject and methods of screening agents for the ability to modulate dissociative and associative states in a subject are further described, it is to be understood that this invention is not limited to a particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited.

It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As used herein the singular forms "a", "an", and "the" include plural referents unless the context clearly dictates otherwise. Thus, for example, reference to "a cell" includes a plurality of such cells and reference to "the agent" includes reference to one or more agents and equivalents thereof, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The term "about," particularly in reference to a given quantity, is meant to encompass deviations of plus or minus five percent.

The term "dissociative disorder" or "disorder of dissociation" as used herein refers to any condition or disease associated with producing a dissociative state in a subject. Dissociative disorders may have various underlying causes, including, but not limited to, a drug, a seizure (e.g., epileptic or nonepileptic), childhood psychological or physical trauma, abuse, a sexual assault, or a dissociation-linked neuropsychiatric disorder, such as, but not limited to, post-traumatic stress disorder (PTSD), borderline personality disorder, or schizophrenia spectrum disorder.

The term "associative disorder" or "disorder of association" as used herein refers to any condition or disease associated with producing an undesirable state of association in a subject. Disorders of association include, without limitation, chronic pain, depression, anxiety, obsessive-compulsive disorder, addiction/dependency, or any dysfunctional association with specific, recurrent, and/or negative thoughts causing morbidity or mortality, wherein disconnecting from the damaging thoughts is beneficial.

"Substantially purified" generally refers to isolation of a substance (compound, drug, inhibitor, agonist, antagonist, polynucleotide, protein, polypeptide, antibody) such that the substance comprises the majority percent of the sample in which it resides. Typically in a sample, a substantially purified component comprises 50%, preferably 80%-85%, more preferably 90-95% of the sample. Techniques for purifying substances of interest are well-known in the art and include, for example, ion-exchange chromatography, affinity chromatography and sedimentation according to density.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with a disorder of dissociation or association) as well as those in which prevention is desired (e.g., those with increased susceptibility to abnormal states of dissociation such as caused by epilepsy or a dissociation-linked neuropsychiatric disorder such as post-traumatic stress disorder (PTSD), borderline personality disorder, or schizophrenia spectrum disorder; or those with increased susceptibility to abnormal states of association such as caused by chronic pain, depression, anxiety, or obsessive-compulsive disorder, etc.).

By "therapeutically effective dose or amount" of an agent that modulates rhythmic neural activity in the posteromedial cortex (e.g., inhibitor or agonist of an HCN pacemaker channel) and/or modulates posteromedial cortical activity (e.g., an agonist or antagonist of a methyl-D-aspartate receptor (NMDAR) or monoamine oxidase) is intended an amount that, when the agent is administered, as described herein, brings about a positive therapeutic response in the treatment of a disorder of dissociation or association. For example, a positive therapeutic response in the treatment of a disorder of dissociation may include a reduction in symptoms of dissociation, such as associated with a seizure or a dissociation-linked neuropsychiatric disorder such as post-traumatic stress disorder (PTSD), borderline personality disorder, or schizophrenia spectrum disorder. A positive therapeutic response in the treatment of a disorder of association may include a reduction in symptoms of association, such as specific, recurrent, and/or negative thoughts that cause morbidity or mortality, associated with chronic pain, depression, anxiety, obsessive-compulsive disorder, addiction/dependency, or other dysfunctional condition, wherein disconnecting from the damaging thoughts associated with the disorder is beneficial. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

The terms "active agent", "agent", "drug", and "pharmacologically active agent" are used interchangeably herein to refer to a chemical material or compound which, when administered to an organism (human or animal) induces a desired pharmacologic and/or physiologic effect by local and/or systemic action.

The term "unit dosage form," as used herein, refers to physically discrete units suitable as unitary dosages for human and animal subjects, each unit containing a predetermined quantity of a compound calculated in an amount sufficient to produce the desired effect in association with a pharmaceutically acceptable diluent, carrier or vehicle. The specifications for unit dosage forms depend on the particular compound employed and the effect to be achieved, and the pharmacodynamics associated with each compound in the host.

"Neural activity" as used herein, may refer to electrical activity of a neuron (e.g., changes in membrane potential of the neuron), as well as indirect measures of the electrical activity of one or more neurons. Thus, neural activity may refer to changes in field potential, changes in intracellular ion concentration (e.g., intracellular calcium concentration), and changes in magnetic resonance induced by electrical activity of neurons, as measured by, e.g., blood oxygenation level dependent (BOLD) signals in functional magnetic resonance imaging.

Modulating Associative and Dissociative Symptoms

The present invention is based on the discovery of a novel therapeutic methodology for modulating associative or dissociative symptoms in a subject. The methods utilize delivery of an of an agent that modulates rhythmic neural activity in the posteromedial cortex of the subject. Without being bound by a particular theory, a posteromedial cortical rhythm is associated with states of dissociation. The rhythmic neural activity depends on local HCN pacemaker channels in the posteromedial cortex. Therefore, direct or indirect modulation of channel activity of HCN pacemaker channels can be used to suppress or induce dissociative symptoms. In addition, posteromedial cortical activity can be stimulated or inhibited by administering modulators of NMDAR channels or monoamine oxidase inhibitors.

In some embodiments, inhibitors of HCN pacemaker channels are used for treating a dissociative disorder. The term "dissociative disorder" or "disorder of dissociation" as used herein refers to any condition or disease associated with producing a dissociative state in a subject. Dissociative disorders may have various underlying causes, including, but not limited to, drug use, seizures (e.g., epileptic or nonepileptic), childhood psychological or physical trauma, abuse, sexual assault, or a dissociation-linked neuropsychiatric disorder, such as, but not limited to, post-traumatic stress disorder (PTSD), borderline personality disorder, or schizophrenia spectrum disorder. At least four isoforms of HCN exist, including HCN1, HCN2, HCN3, or HCN4. Thus, in certain embodiments one or more of the isoforms HCN1, HCN2, HCN3, or HCN4, or any combination thereof, are inhibited. Preferably, at least HCN1 is inhibited by the HCN inhibitor. Inhibition may be complete or partial (i.e., all activity, some activity, or most activity is blocked by an inhibitor). For example, an inhibitor may reduce the activity of HCN by 10%, 20%, 30%, 40%, 50%, 60%, 70%, 80%, 90%, 100%, or any amount in between as compared to native or control levels. Exemplary inhibitors of HCN pacemaker channels include, without limitation, gabapentin, ivabradine, amiodarone, clonidine, loperamide, bepridil, zatebradine, cilobradine, alinidine, falipamil, ZD7288, CP-339,818, and YS-035.

In some embodiments, direct or indirect agonists of HCN pacemaker channels are used to induce a dissociative state in a subject who is suffering from painful or damaging symptoms of a disorder of association. For example, in subjects who have chronic pain, an overwhelming association with pain can persist even when the original source of the pain no longer exists (e.g., pain from a limb that has been amputated). In conditions such as depression, anxiety, obsessive-compulsive disorder, addiction and dependency, dysfunctional association with specific, recurrent, and/or negative thoughts can cause morbidity or mortality, wherein disconnecting from the damaging thoughts is beneficial.

Exemplary agonists of HCN pacemaker channels include, without limitation, lamotrigine, cyclic adenosine monophosphate (cAMP) and derivatives thereof, cyclic cytosine monophosphate (cCMP) and derivatives thereof, cyclic inosine monophosphate (cIMP) and derivatives thereof, and neuromodulators causing hyperpolarization of HCN channels.

Exemplary agents that modulate posteromedial cortical activity include, without limitation, lidocaine, bupivacaine, propofol, a benzodiazepine, and a barbiturate.

Exemplary agents that modulate an NMDAR include, without limitation, ketamine, dextromethorphan (DXM), phencyclidine (PCP), methoxetamine (MXE), pethidine, levorphanol, methadone, dextropropoxyphene, tramadol, ketobemidone, and etoxadrol.

Exemplary agents that modulate a monoamine oxidase include, without limitation, isocarboxazid, hydracarbazine, phenelzine, tranylcypromine, bifemelane, moclobemide, pirlindole, rasagiline, selegiline, and safinamide.

Pharmaceutical Compositions

Pharmaceutical compositions comprising an agent that modulates an HCN pacemaker channel, N-methyl-D-aspartate receptor (NMDAR), or monoamine oxidase, and/or other agent that modulates posteromedial cortical activity can be formulated into pharmaceutical compositions optionally comprising one or more pharmaceutically acceptable excipients. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerine, vegetable oils, phospholipids, and surfactants. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof.

A composition can also include an antimicrobial agent for preventing or deterring microbial growth. Nonlimiting examples of antimicrobial agents include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the agent (e.g., that modulates an HCN pacemaker channel, N-methyl-D-aspartate receptor (NMDAR), or monoamine oxidase, and/or other agent that modulates posteromedial cortical activity), or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (BASF, Mount Olive, New Jersey); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as EDTA; and zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the agent (e.g., that modulates an HCN pacemaker channel, N-methyl-D-aspartate receptor (NM-DAR), or monoamine oxidase, and/or other agent that modulates posteromedial cortical activity) in the composition will vary depending on a number of factors, but will optimally be a therapeutically effective dose when the composition is in a unit dosage form or container (e.g., a vial). A therapeutically effective dose can be determined experimentally by repeated administration of increasing amounts of the composition in order to determine which amount produces a clinically desired endpoint.

The amount of any individual excipient in the composition will vary depending on the nature and function of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the composition in an amount of about 1% to about 99% by weight, preferably from about 5% to about 98% by weight, more preferably from about 15 to about 95% by weight of the excipient, with concentrations less than 30% by weight most preferred. These foregoing pharmaceutical excipients along with other excipients are described in "Remington: The Science & Practice of Pharmacy", 19th ed., Williams & Williams, (1995), the "Physician's Desk Reference", 52nd ed., Medical Economics, Montvale, NJ (1998), and Kibbe, A. H., Handbook of Pharmaceutical Excipients, 3rd Edition, American Pharmaceutical Association, Washington, D.C., 2000.

The compositions encompass all types of formulations and in particular those that are suited for injection, e.g., powders or lyophilates that can be reconstituted with a solvent prior to use, as well as ready for injection solutions or suspensions, dry insoluble compositions for combination with a vehicle prior to use, and emulsions and liquid concentrates for dilution prior to administration. Examples of suitable diluents for reconstituting solid compositions prior to injection include bacteriostatic water for injection, dextrose 5% in water, phosphate buffered saline, Ringer's solution, saline, sterile water, deionized water, and combinations thereof. With respect to liquid pharmaceutical compositions, solutions and suspensions are envisioned. Additional preferred compositions include those for oral, ocular, or localized delivery.

The pharmaceutical preparations herein can also be housed in a syringe, an implantation device, or the like, depending upon the intended mode of delivery and use. Preferably, the compositions comprising the agent (e.g., that modulates an HCN pacemaker channel, N-methyl-D-aspartate receptor (NMDAR), or monoamine oxidase, and/or other agent that modulates posteromedial cortical activity) or a derivative thereof are in unit dosage form, meaning an amount of a composition appropriate for a single dose, in a premeasured or pre-packaged form.

The compositions herein may optionally include one or more additional agents, such as other medications for treating a disorder of dissociation or association, or other condition. Compounded preparations may include an agent that modulates an HCN pacemaker channel, N-methyl-D-aspartate receptor (NMDAR), or monoamine oxidase, and/or other agent that modulates posteromedial cortical activity, and one or more other agents for treating a disease or disorder associated with association or disassociation, such as, but not limited to, anti-epileptic medications, benzodiazepines (e.g., lorazepam, diazepam and midazolam), anti-depressants (e.g., selective serotonin reuptake inhibitors (SSRIs), serotonin-norepinephrine reuptake inhibitors (SNRIs), and tricyclic antidepressants), glucocorticoids, and the like.

Alternatively, such agents can be contained in a separate composition from the composition comprising the agent that modulates an HCN pacemaker channel, N-methyl-D-aspartate receptor (NMDAR), or monoamine oxidase, and/or other agent that modulates posteromedial cortical activity, and co-administered concurrently, before, or after the composition comprising the agent that modulates an HCN pacemaker channel, N-methyl-D-aspartate receptor (NMDAR), or monoamine oxidase, and/or other agent that modulates posteromedial cortical activity.

Administration

At least one therapeutically effective cycle of treatment with a composition comprising an agent that modulates an HCN pacemaker channel, N-methyl-D-aspartate receptor (NMDAR), or monoamine oxidase, and/or other agent that modulates posteromedial cortical activity, as described herein, will be administered to a subject for treatment of a disorder of dissociation or association.

Disorders of dissociation include any condition or disease associated with producing a dissociative state in a subject. Dissociative disorders may have various underlying causes, including, but not limited to, drug use, seizures (e.g., epileptic or nonepileptic), childhood psychological or physical trauma, abuse, sexual assault, or a dissociation-linked neuropsychiatric disorder, such as, but not limited to, post-traumatic stress disorder (PTSD), borderline personality disorder, or schizophrenia spectrum disorder.

Disorders of association include any condition or disease associated with producing an undesirable state of association in a subject. Disorders of association include, without limitation, chronic pain, depression, anxiety, obsessive-compulsive disorder, addiction/dependency, or any dysfunctional association with specific, recurrent, and/or negative thoughts causing morbidity or mortality, wherein disconnecting from the damaging thoughts is beneficial.

By "therapeutically effective dose or amount" of an agent that modulates rhythmic neural activity in the posteromedial cortex (e.g., inhibitor or agonist of an HCN pacemaker channel) and/or modulates posteromedial cortical activity (e.g., an agonist or antagonist of a methyl-D-aspartate receptor (NMDAR) or monoamine oxidase) is intended an amount that, when the agent is administered, as described herein, brings about a positive therapeutic response in the treatment of a disorder of dissociation or association. For example, a positive therapeutic response in the treatment of a disorder of dissociation may include a reduction in symptoms of dissociation, such as associated with a seizure or a dissociation-linked neuropsychiatric disorder such as post-traumatic stress disorder (PTSD), borderline personality disorder, or schizophrenia spectrum disorder. A positive therapeutic response in the treatment of a disorder of association may include a reduction in symptoms of association, such as specific, recurrent, and/or negative thoughts that cause morbidity or mortality, associated with chronic pain, depression, anxiety, obsessive-compulsive disorder, addiction/dependency, or other dysfunctional condition, wherein disconnecting from the damaging thoughts associated with the disorder is beneficial. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

In certain embodiments, multiple therapeutically effective doses of compositions comprising the agent that modulates an HCN pacemaker channel, N-methyl-D-aspartate receptor (NMDAR), or monoamine oxidase, and/or other agent that modulates posteromedial cortical activity, and/or one or more other therapeutic agents, such as one or more other agents for treating a disorder of dissociation or association, such as, but not limited to, anti-epileptic medications, benzodiazepines (e.g., lorazepam, diazepam and midazolam), antidepressants (e.g., selective serotonin reuptake inhibitors (SSRIs), serotonin-norepinephrine reuptake inhibitors (SNRIs), and tricyclic antidepressants), glucocorticoids, or other medications will be administered. The compositions comprising the agent (e.g., that modulates an HCN pacemaker channel, N-methyl-D-aspartate receptor (NMDAR), or monoamine oxidase, and/or other agent that modulates posteromedial cortical activity) are typically, although not necessarily, administered orally, via injection (subcutaneously, intravenously, or intramuscularly), by infusion, or locally. Additional modes of administration are also contemplated, such as intraperitoneally, intracranially, intrathecal, pulmonary, and so forth.

The preparations according to the invention are also suitable for local treatment. For example, compositions comprising the agent (e.g., that modulates an HCN pacemaker channel, N-methyl-D-aspartate receptor (NMDAR), or monoamine oxidase, and/or other agent that modulates posteromedial cortical activity) may be administered by intracranial injection or stereotactic injection into the posteromedial cortex. The particular preparation and appropriate method of administration can be chosen to target the agent to the posteromedial cortex. Local treatment may avoid some side effects of systemic therapy.

The pharmaceutical preparation can be in the form of a liquid solution or suspension immediately prior to administration, but may also take another form such as a syrup, cream, ointment, tablet, capsule, powder, gel, matrix, suppository, or the like. The pharmaceutical compositions comprising the agent (e.g., that modulates an HCN pacemaker channel, N-methyl-D-aspartate receptor (NMDAR), or monoamine oxidase, and/or other agent that modulates posteromedial cortical activity), and/or other agents may be administered using the same or different routes of administration in accordance with any medically acceptable method known in the art.

In another embodiment, the pharmaceutical compositions comprising the agent (e.g., that modulates an HCN pacemaker channel, N-methyl-D-aspartate receptor (NMDAR), or monoamine oxidase, and/or other agent that modulates posteromedial cortical activity) and/or other agents are administered prophylactically, e.g., to prevent a dissociative state or associative state. Such prophylactic uses will be of particular value for subjects who have epilepsy or a dissociation-linked neuropsychiatric disorders such as post-traumatic stress disorder (PTSD), borderline personality disorder, or schizophrenia spectrum disorder to prevent a dissociative state, or subjects who have chronic pain, depression, anxiety, obsessive-compulsive disorder, addiction/dependency to prevent specific, recurrent, and/or negative thoughts causing morbidity or mortality, In another embodiment, the pharmaceutical compositions comprising the agent (e.g., that modulates an HCN pacemaker channel, N-methyl-D-aspartate receptor (NMDAR), or monoamine oxidase, and/or other agent that modulates posteromedial cortical activity) and/or other agents are in a sustained-release formulation, or a formulation that is administered using a sustained-release device. Such devices are well known in the art, and include, for example, transdermal patches, and miniature implantable pumps that can provide for drug delivery over time in a continuous, steady-state fashion at a variety of doses to achieve a sustained-release effect with a non-sustained-release pharmaceutical composition.

Those of ordinary skill in the art will appreciate which conditions the agent (e.g., that modulates an HCN pacemaker channel, N-methyl-D-aspartate receptor (NMDAR), or monoamine oxidase, and/or other agent that modulates posteromedial cortical activity) can effectively treat. The actual dose to be administered will vary depending upon the age, weight, and general condition of the subject as well as the severity of the condition being treated, the judgment of the health care professional, and conjugate being administered. Therapeutically effective amounts can be determined by those skilled in the art, and will be adjusted to the particular requirements of each particular case.

In certain embodiments, multiple therapeutically effective doses of a composition comprising the agent (e.g., that modulates an HCN pacemaker channel, N-methyl-D-aspartate receptor (NMDAR), or monoamine oxidase, and/or other agent that modulates posteromedial cortical activity) will be administered according to a daily dosing regimen or intermittently. For example, a therapeutically effective dose can be administered, one day a week, two days a week, three days a week, four days a week, or five days a week, and so forth. By "intermittent" administration is intended the therapeutically effective dose can be administered, for example, every other day, every two days, every three days, once a week, every other week, and so forth. For example, in some embodiments, a composition comprising the agent that modulates an HCN pacemaker channel, N-methyl-D-aspartate receptor (NMDAR), or monoamine oxidase will be administered once-weekly, twice-weekly or thrice-weekly for an extended period of time, such as for 1, 2, 3, 4, 5, 6, 7, 8 . . . 10 . . . 15 . . . 24 weeks, and so forth. By "twice-weekly" or "two times per week" is intended that two therapeutically effective doses of the agent in question is administered to the subject within a 7 day period, beginning on day 1 of the first week of administration, with a minimum of 72 hours, between doses and a maximum of 96 hours between doses. By "thrice weekly" or "three times per week" is intended that three therapeutically effective doses are administered to the subject within a 7 day period, allowing for a minimum of 48 hours between doses and a maximum of 72 hours between doses. For purposes of the present invention, this type of dosing is referred to as "intermittent" therapy. In accordance with the methods of the present invention, a subject can receive intermittent therapy (i.e., once-weekly, twice-weekly or thrice-weekly administration of a therapeutically effective dose) for one or more weekly cycles until the desired therapeutic response is achieved. The agents can be administered by any acceptable route of administration as noted herein below. The amount administered will depend on the potency of the agent that modulates an HCN pacemaker channel, N-methyl-D-aspartate receptor (NMDAR), or monoamine oxidase or the derivative thereof and/or other agents administered, the magnitude of the effect desired, and the route of administration.

The agent (e.g., that modulates an HCN pacemaker channel, N-methyl-D-aspartate receptor (NMDAR), or monoamine oxidase, and/or other agent that modulates posteromedial cortical activity) or a derivative thereof (again, preferably provided as part of a pharmaceutical preparation) can be administered alone or in combination with one or more other therapeutic agents, such as other agents for treating a disorder of dissociation or association, such as, but not limited to, anti-epileptic medications, benzodiazepines (e.g., lorazepam, diazepam and midazolam), antidepressants (e.g., selective serotonin reuptake inhibitors (SSRIs), serotonin-norepinephrine reuptake inhibitors (SNRIs), and tricyclic antidepressants), glucocorticoids, or other medications used to treat a particular condition or disease according to a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Preferred compositions are those requiring dosing no more than once a day.

The agent (e.g., that modulates an HCN pacemaker channel, N-methyl-D-aspartate receptor (NMDAR), or monoamine oxidase, and/or other agent that modulates posteromedial cortical activity) or a derivative thereof can be administered prior to, concurrent with, or subsequent to other agents. If provided at the same time as other agents, the agent that modulates an HCN pacemaker channel, N-methyl-D-aspartate receptor (NMDAR), or monoamine oxidase, and/or other agent that modulates posteromedial cortical activity can be provided in the same or in a different composition. Thus, the agent that modulates an HCN pacemaker channel, N-methyl-D-aspartate receptor (NMDAR), or monoamine oxidase, and/or other agent that modulates posteromedial cortical activity and one or more other agents can be presented to the individual by way of concurrent therapy. By "concurrent therapy" is intended administration to a subject such that the therapeutic effect of the combination of the substances is caused in the subject undergoing therapy. For example, concurrent therapy may be achieved by administering a dose of a pharmaceutical composition comprising the agent that modulates an HCN pacemaker channel, N-methyl-D-aspartate receptor (NMDAR), or monoamine oxidase, and/or other agent that modulates posteromedial cortical activity and a dose of a pharmaceutical composition comprising at least one other agent, such as another drug for treating a disorder of dissociation or association, which in combination comprise a therapeutically effective dose, according to a particular dosing regimen. Similarly, the agent that modulates an HCN pacemaker channel, N-methyl-D-aspartate receptor (NMDAR), or monoamine oxidase, and/or other agent that modulates posteromedial cortical activity and one or more other therapeutic agents can be administered in at least one therapeutic dose. Administration of the separate pharmaceutical compositions can be performed simultaneously or at different times (i.e., sequentially, in either order, on the same day, or on different days), as long as the therapeutic effect of the combination of these substances is caused in the subject undergoing therapy.

Toxicity can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in further optimizing and/or defining a therapeutic dosage range and/or a sub-therapeutic dosage range (e.g., for use in humans). The exact formulation, route of administration and dosage can be chosen by the individual physician in view of the patient's condition.

Additionally, treatment with the agent that modulates an HCN pacemaker channel, N-methyl-D-aspartate receptor (NMDAR), or monoamine oxidase, and/or other agent that modulates posteromedial cortical activity may be combined with any other medical treatment for a disorder of disassociation or association, such as, but not limited to, administering anti-epileptic medications, benzodiazepines (e.g., lorazepam, diazepam and midazolam), antidepressants (e.g., selective serotonin reuptake inhibitors (SSRIs), serotonin-norepinephrine reuptake inhibitors (SNRIs), and tricyclic antidepressants), glucocorticoids.

Screening to Determine if an Agent Induces or Suppresses Dissociative Symptoms

The inventors have discovered that rhythmic neural activity in the posteromedial cortex is associated with dissociative symptoms. Accordingly, screening methods for identifying candidate agents that induce or inhibit rhythmic neural activity in the posteromedial cortex are provided.

Detection of rhythmic neural activity in the posteromedial cortex may be performed by any method known in the art. For example, functional brain imaging of neural activity in the posteromedial cortex may be carried out by electrical methods such as electrocorticography (ECoG), electroencephalography (EEG), stereoelectroencephalography (sEEG), magnetoencephalography (MEG), single photon emission computed tomography (SPECT), as well as metabolic and blood flow studies such as functional magnetic resonance imaging (fMRI), and positron emission tomography (PET). In some embodiments, the left and right posteromedial cortex regions are mapped to determine optimal positioning for electrodes to detect rhythmic neural activity associated with a dissociative state. One or more posteromedial cortex regions may be implanted with electrodes to detect rhythmic neural activity associated with a dissociative state.

A variety of different test agents may be screened. Candidate agents encompass numerous chemical classes, e.g., small organic compounds having a molecular weight of more than 50 daltons and less than about 10,000 daltons, less than about 5,000 daltons, or less than about 2,500 daltons. Test agents can comprise functional groups necessary for structural interaction with proteins, e.g., hydrogen bonding, and can include at least an amine, carbonyl, hydroxyl or carboxyl group, or at least two of the functional chemical groups. The test agents can comprise cyclical carbon or heterocyclic structures and/or aromatic or polyaromatic structures substituted with one or more of the above functional groups. Test agents are also found among biomolecules including peptides, saccharides, fatty acids, steroids, purines, pyrimidines, derivatives, structural analogs or combinations thereof.

Test agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Moreover, screening may be directed to known pharmacologically active compounds or drugs and chemical analogs thereof, or to new agents with unknown properties such as those created through rational drug design.

In some embodiments, test agents are synthetic compounds. A number of techniques are available for the random and directed synthesis of a wide variety of organic compounds and biomolecules, including expression of randomized oligonucleotides. See for example WO 94/24314, hereby expressly incorporated by reference, which discusses methods for generating new compounds, including random chemistry methods as well as enzymatic methods.

In another embodiment, the test agents are provided as libraries of natural compounds in the form of bacterial, fungal, plant and animal extracts that are available or readily produced. Additionally, natural or synthetically produced libraries and compounds are readily modified through conventional chemical, physical and biochemical means. Known pharmacological agents may be subjected to directed or random chemical modifications, including enzymatic modifications, to produce structural analogs.

In some embodiments, the test agents are organic moieties. In this embodiment, test agents are synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepins, beta-lactams, tetracylines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or candidate agents which can then be tested using the present invention.

In some embodiments test agents are assessed for any cytotoxic activity it may exhibit toward a living eukaryotic cell, using well-known assays, such as trypan blue dye exclusion, an MTT (3-(4,5-dimethylthiazol-2-yl)-2,5-diphenyl-2 H-tetrazolium bromide) assay, and the like. Agents that do not exhibit significant cytotoxic activity are considered candidate agents.

In some embodiments, the test agent is an antibody that specifically binds to and inhibits biological activity of an HCN pacemaker channel. Any type of antibody may be screened for the ability to inhibit HCN and rhythmic neural activity in the posteromedial cortex by the methods described herein, including polyclonal antibodies, monoclonal antibodies, hybrid antibodies, altered antibodies, chimeric antibodies, and humanized antibodies, as well as: hybrid (chimeric) antibody molecules (see, for example, Winter et al. (1991) Nature 349:293-299; and U.S. Pat. No. 4,816, 567); F(ab')₂ and F(ab) fragments; F_v molecules (noncovalent heterodimers, see, for example, Inbar et al. (1972) Proc Nat/Acad Sci USA 69:2659-2662; and Ehrlich et al. (1980) Biochem 19:4091-4096); single-chain Fv molecules (sFv) (see, e.g., Huston et al. (1988) Proc Natl Acad Sci USA 85:5879-5883); nanobodies or single-domain antibodies (sdAb) (see, e.g., Wang et al. (2016) Int J Nanomedicine 11:3287-3303, Vincke et al. (2012) Methods Mol Biol 911: 15-26; dimeric and trimeric antibody fragment constructs; minibodies (see, e.g., Pack et al. (1992) Biochem 31:1579-1584; Cumber et al. (1992) J Immunology 149B:120-126); humanized antibody molecules (see, e.g., Riechmann et al. (1988) Nature 332:323-327; Verhoeyan et al. (1988) Science 239:1534-1536; and U.K. Patent Publication No. GB 2,276, 169, published 21 Sep. 1994); and, any functional fragments obtained from such molecules, wherein such fragments retain specific-binding properties of the parent antibody molecule.

In other embodiments, the test agent is an aptamer that specifically binds to and inhibits biological activity of a HCN pacemaker channel. Aptamers may be isolated from a combinatorial library and improved by directed mutation or repeated rounds of mutagenesis and selection. For a description of methods of producing aptamers, see, e.g., Aptamers: Tools for Nanotherapy and Molecular Imaging (R. N. Veedu ed., Pan Stanford, 2016), Nucleic Acid and Peptide Aptamers: Methods and Protocols (Methods in Molecular Biology, G. Mayer ed., Humana Press, 2009), Aptamers Selected by Cell-SELEX for Theranostics (W. Tan, X. Fang eds., Springer, 2015), Cox et al. (2001) Bioorg. Med. Chem. 9(10):2525-2531; Cox et al. (2002) Nucleic Acids Res. 30(20): el 08, Kenan et al. (1999) Methods Mol. Biol. 118:217-231; Platella et al. (2016) Biochim. Biophys. Acta Nov 16 pii: S0304-4165(16)30447-0, and Lyu et al. (2016) Theranostics 6(9):1440-1452; herein incorporated by reference in their entireties.

In yet other embodiments, the test agent is an antibody mimetic that specifically binds to and inhibits biological activity of an HCN1 pacemaker channel. Any type of antibody mimetic may be used, including, but not limited to, affibody molecules (Nygren (2008) FEBS J. 275 (11):2668-2676), affilins (Ebersbach et al. (2007) J. Mol. Biol. 372 (1):172-185), affimers (Johnson et al. (2012) Anal. Chem. 84 (15):6553-6560), affitins (Krehenbrink et al. (2008) J. Mol. Biol. 383 (5):1058-1068), alphabodies (Desmet et al. (2014) Nature Communications 5:5237), anticalins (Skerra (2008) FEBS J. 275 (11):2677-2683), avimers (Silverman et al. (2005) Nat. Biotechnol. 23 (12):1556-1561), darpins (Stumpp et al. (2008) Drug Discov. Today 13 (15-16):695-701), fynomers (Grabulovski et al. (2007) J. Biol. Chem. 282 (5):3196-3204), and monobodies (Koide et al. (2007) Methods Mol. Biol. 352:95-109).

In some embodiments, the method further comprises administering a dissociative agent (e.g., ketamine or phencyclidine) that induces rhythmic neural activity in the posteromedial cortex; and detecting whether the candidate agent suppresses the rhythmic neural activity induced by the dissociative agent.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-28 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A composition comprising an inhibitor of a hyperpolarization-activated cyclic nucleotide-gated (HCN) pacemaker channel for use in treatment of a dissociative disorder.
2. The composition of aspect 1, wherein the inhibitor of the HCN pacemaker channel is gabapentin, ivabradine, amiodarone, clonidine, loperamide, bepridil, zatebradine, cilobradine, alinidine, falipamil, ZD7288, CP-339,818, or YS-035.
3. The composition of aspect 1 or 2, wherein the HCN pacemaker channel is a HCN1, HCN2, HCN3, or HCN4 isoform.
4. The composition of any one of aspects 1-3, further comprising a pharmaceutically acceptable excipient.
5. The composition of any one of aspects 1-4, wherein the dissociative disorder is caused by a drug, a seizure, childhood psychological or physical trauma, abuse, sexual assault, or a dissociation-linked neuropsychiatric disorder.
6. The composition of aspect 5, wherein the dissociation-linked neuropsychiatric disorder is post-traumatic stress disorder (PTSD), borderline personality disorder, or schizophrenia spectrum disorder.
7. A method of treating a subject for a dissociative disorder, the method comprising administering a therapeutically effective amount of an inhibitor of a hyperpolarization-activated cyclic nucleotide-gated (HCN) pacemaker channel to the subject.
8. The method of aspect 7, wherein the inhibitor is gabapentin, ivabradine, amiodarone, clonidine, loperamide, bepridil, zatebradine, cilobradine, alinidine, falipamil, ZD7288, CP-339,818, or YS-035.
9. The composition of aspect 7 or 8, wherein the HCN pacemaker channel is a HCN1, HCN2, HCN3, or HCN4 isoform.
10. The method of any one of aspects 7-9, wherein the dissociative disorder is caused by a drug, a seizure, childhood psychological or physical trauma, abuse, sexual assault, or a dissociation-linked neuropsychiatric disorder.
11. The method of aspect 10, wherein the dissociation-linked neuropsychiatric disorder is post-traumatic stress disorder (PTSD), borderline personality disorder, or schizophrenia spectrum disorder.
12. The method of any one of aspects 7-11, wherein the inhibitor is administered orally, intravenously, intramuscularly, intraperitoneally, intracranially, or locally.
13. The method of any one of aspects 7-12, wherein the agent is administered daily or intermittently.
14. The method of any one of aspects 7-13, wherein the subject is human.
15. A method of modulating associative or dissociative symptoms in a subject, the method comprising administering an effective amount of an agent that modulates rhythmic neural activity in the posteromedial cortex of the subject.
16. The method of aspect 15, wherein the agent is selected from the group consisting of an agent that modulates an HCN pacemaker channel, an agent that modulates an N-methyl-D-aspartate receptor (NMDAR), an agent that modulates posteromedial cortical activity, and a monoamine oxidase inhibitor.
17. The method of aspect 15, wherein the agent that modulates an HCN pacemaker channel is gabapentin, lamotrigine, ivabradine, amiodarone, clonidine, or loperamide.
18. The method of aspect 15, wherein the HCN pacemaker channel is a HCN1, HCN2, HCN3, or HCN4 isoform.
19. The method of aspect 15, wherein the agent that modulates posteromedial cortical activity is lidocaine, bupivacaine, propofol, a benzodiazepine, or a barbiturate.
20. The method of aspect 15, wherein the agent that modulates the NMDAR is ketamine, dextromethorphan (DXM), phencyclidine (PCP), methoxetamine (MXE), pethidine, levorphanol, methadone, dextropropoxyphene, tramadol, ketobemidone, or etoxadrol.
21. The method of aspect 15, wherein the monoamine oxidase inhibitor is isocarboxazid, hydracarbazine, phenelzine, tranylcypromine, bifemelane, moclobemide, pirlindole, rasagiline, selegiline, or safinamide.
22. The method of any one of aspects 15-21, wherein the agent is administered orally, intravenously, intramuscularly, intraperitoneally, intracranially, or locally.
23. The method of any one of aspects 15-23, wherein the agent is administered daily or intermittently.
24. The method of any one of aspects 15-23, wherein the subject has a dissociative disorder caused by a drug, a seizure, childhood psychological or physical trauma, abuse, or a sexual assault, post-traumatic stress disorder (PTSD), borderline personality disorder, schizophrenia spectrum disorder, or chronic pain.
25. A method of screening a candidate agent to determine if the candidate agent induces or inhibits a dissociative state in a subject, the method comprising:
a) administering the candidate agent to the subject; and
b) detecting whether the candidate agent induces or inhibits rhythmic neural activity in the posteromedial cortex of the subject.
26. The method of aspect 25, wherein said detecting the rhythmic neural activity in the posteromedial cortex of the subject comprises performing electrocorticography (ECoG), electroencephalography (EEG), stereoelectroencephalography (sEEG), magnetoencephalography (MEG), single photon emission computed tomography (SPECT), functional magnetic resonance imaging (fMRI), or positron emission tomography (PET).
27. The method of aspect 25 or 26, further comprising administering a dissociative agent that induces rhythmic neural activity in the posteromedial cortex; and detecting whether the candidate agent inhibits the rhythmic neural activity induced by the dissociative agent.
28. The method of aspect 27, wherein the dissociative agent is ketamine or phencyclidine.

Experimental

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

Example 1

Deep Posteromedial Cortical Rhythm Underlying Dissociation

Here we investigate the dissociative-like behavioral state with high-speed brain-wide approaches in both mouse and human, identifying underlying deep posteromedial-cortex rhythmic dynamics along with molecular, cellular, and physiological mechanisms.

Advanced imaging methods allow cell type-specific recording of neural activity across the mammalian brain, enabling exploration of how brain-wide dynamical patterns give rise to complex behavioral states[1-12]. Dissociation is an altered behavioral state with unknown underlying neurophysiology but substantial basic and clinical significance—that can occur with trauma, epilepsy, or dissociative drug use[13,14]—in which the integrity of experience is disrupted, and reproducible cognitive phenomena result (including dissociation of stimulus detection from stimulus-related affective responses). Here we have established such a dissociation-like state in mice, using precisely-dosed ketamine or phencyclidine. Large-scale imaging of neural activity revealed that these dissociative agents elicited a 1-3 Hz rhythm in retrosplenial cortex layer-5 neurons. Electrophysiological recording with four simultaneously-deployed high-density probes revealed rhythmic coupling of retrosplenial cortex and anatomically-connected anterior thalamus circuitry, but uncoupling from most other brain regions, including an inverse correlation with frontally-projecting thalamic nuclei. In testing for causal significance, rhythmic optogenetic activation of retrosplenial cortex layer-5 neurons recapitulated the dissociation-like behavioral effects. Local retrosplenial HCN1 pacemaker channels were required for systemic ketamine to induce this rhythm and to elicit dissociation-like behavioral effects. In a patient with focal epilepsy, simultaneous intracranial stereo-EEG recordings from across the brain revealed a similarly-localized rhythm in the homologous deep posteromedial cortex temporally correlated with pre-seizure self-reported dissociation, and local brief electrical stimulation elicited dissociative experiences. These results identify molecular, cellular, and physiological properties of a conserved deep posteromedial cortical rhythm underlying states of dissociation.

Results

Figure 1D:
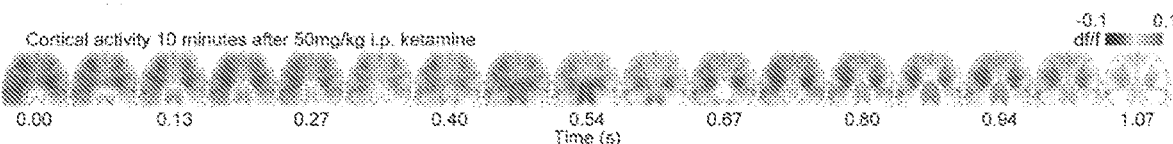
Figure 1E:
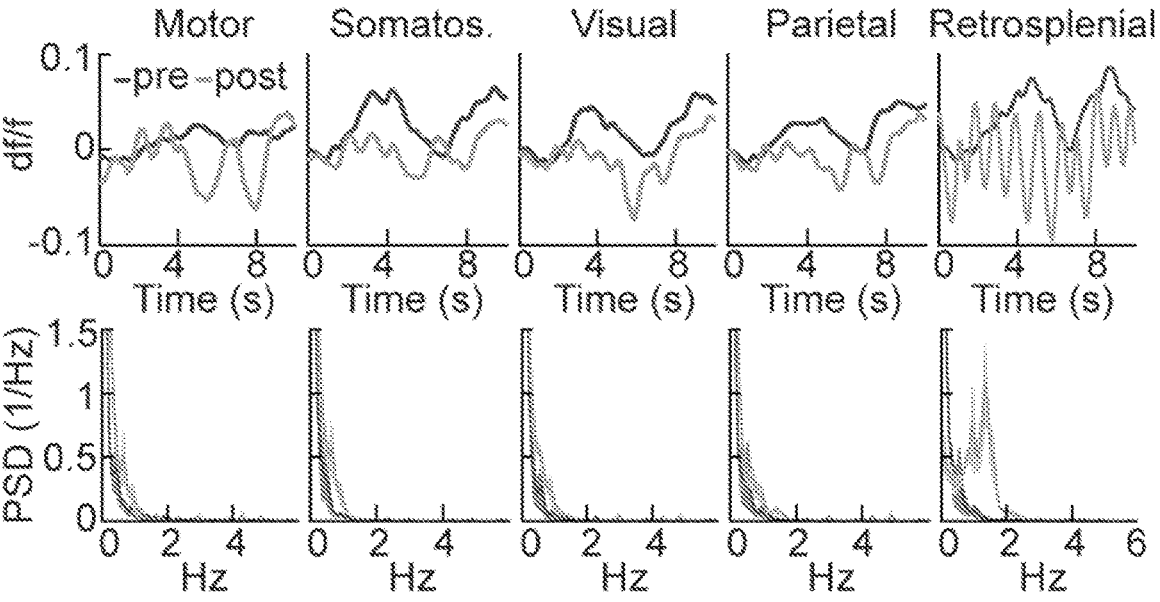
Figure 1F:
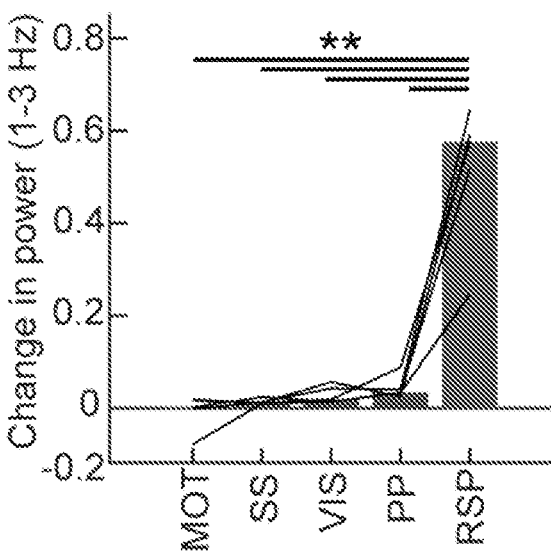
Figure 1G:
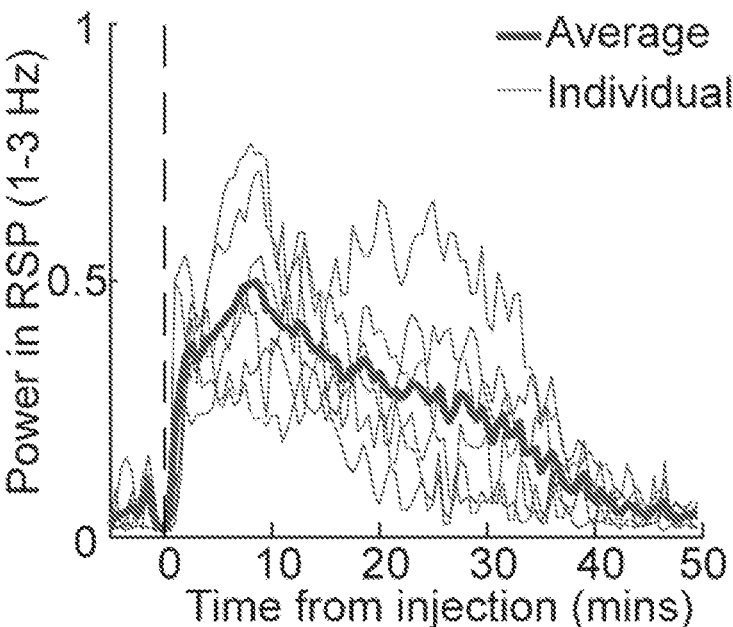
Figure 1H:
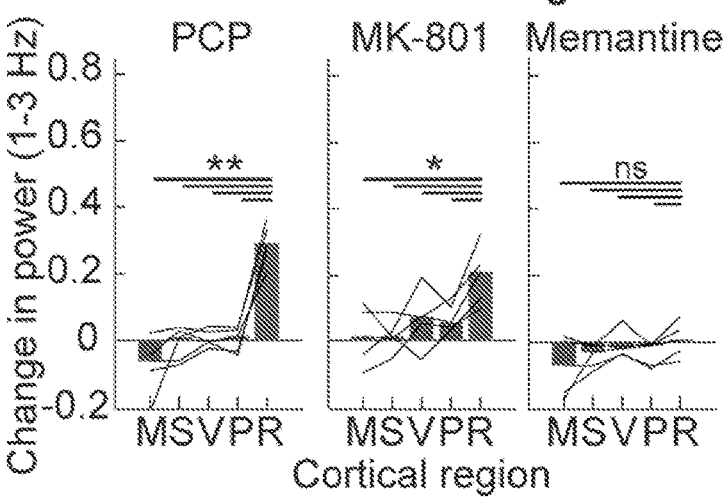

Multiregional Imaging Reveals Ketamine-Induced Rhythm Restricted to Retrosplenial Cortex We recorded multiregional neuronal activity by leveraging widefield microscopy, a cleared skull preparation, and atlas registration in GCaMP6s-expressing mice (FIGS. 1A-1C)[6,8,15]. Upon intraperitoneal injection of ketamine (50 mg/kg subanesthetic dose; Methods), a 1-3 Hz oscillation emerged in retrosplenial cortex (RSP), but not in any other cortical region (FIGS. 1D-1 F, FIG. 6a; n=5 mice). The rhythm emerged within 120 seconds, returned to baseline after ~45 minutes (FIG. 1G, Extended Data FIGS. 1B-1E), and exhibited similar magnitude across five consecutive days; no ketamine-induced 1-3 Hz movements were observed (FIGS. 6G-6L). Subanesthetic ketamine reduced RSP activity-correlations with all other dorsal-cortical regions (FIG. 6J). Using high-magnification two-photon microscopy we imaged superficial neuropil through a glass-covered cranial window, and observed the oscillation in RSP but not neighboring visual cortex (FIGS. 6K-6O; n=4 mice, paired t-test p=0.027).

In humans, ketamine can cause dissociation, analgesia, hallucinations, sedation, and anesthesia. To test whether other drugs with or without dissociative properties elicited similar cortical activity patterns, we repeated imaging with NMDAR-antagonists, a hallucinogen, anesthetics, a sedative, and an analgesic. PCP, a dissociative NMDAR-antagonist like ketamine, induced the RSP-localized oscillation (FIG. 1H), as did MK-801, a long-lasting dissociative NMDAR-antagonist. Memantine, a low-affinity uncompetitive NMDAR-antagonist with a non-dissociative clinical profile did not elicit oscillation, nor did saline or lysergic acid diethylamide (LSD) (FIG. 7). Non-dissociative anesthetics dexmedetomidine, propofol and the commonly-used veterinary ketamine/xylazine cocktail, elicited waves of cortical activity without RSP restriction (FIG. 8). Neither the GABAergic sedative diazepam nor the centrally-acting opioid-analgesic buprenorphine elicited the rhythm (FIG. 9). Together, these data revealed an oscillatory pattern spatially restricted to RSP selectively induced by dissociative agents.

Retrosplenial Oscillation Localized to Layer 5 Neurons

Figure 1I:
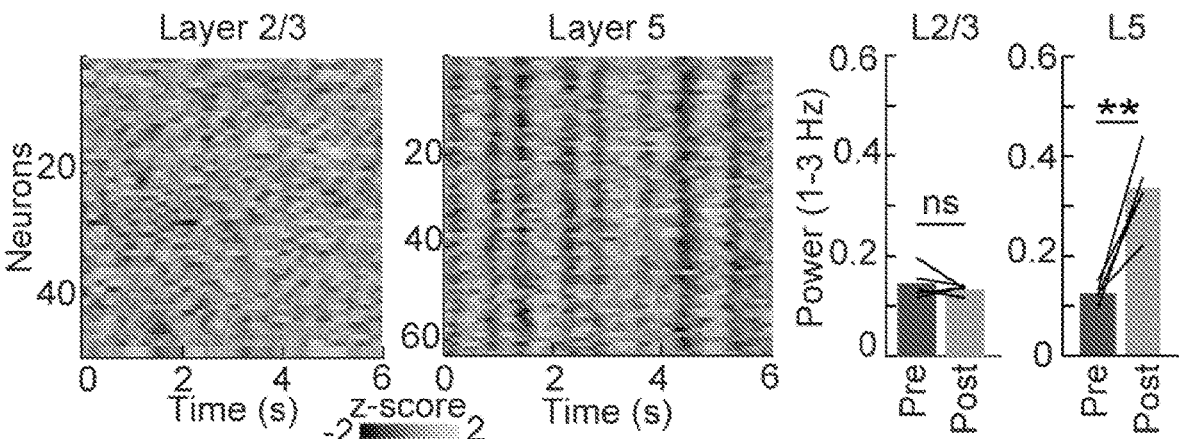
Figure 1J:
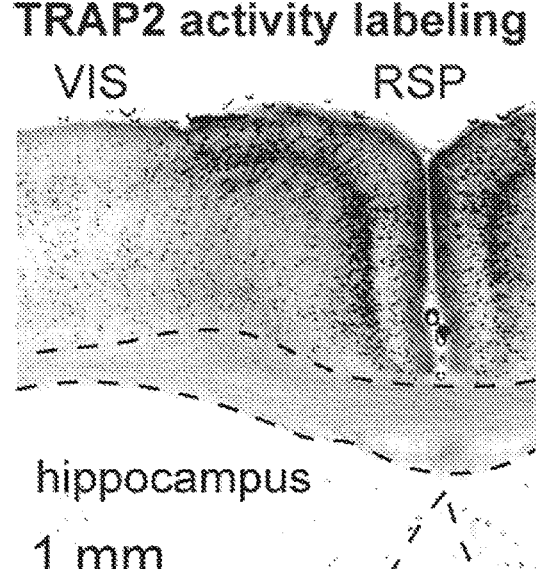
Figure 5A:
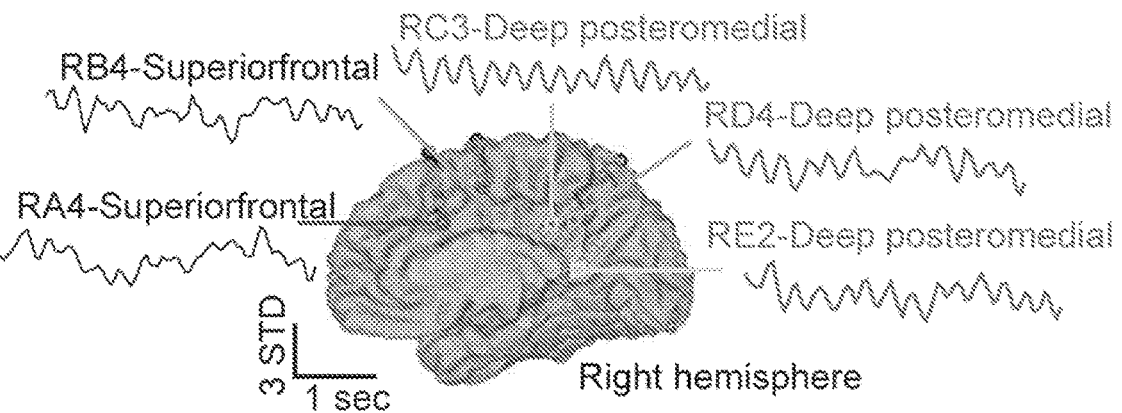
Figure 5A:
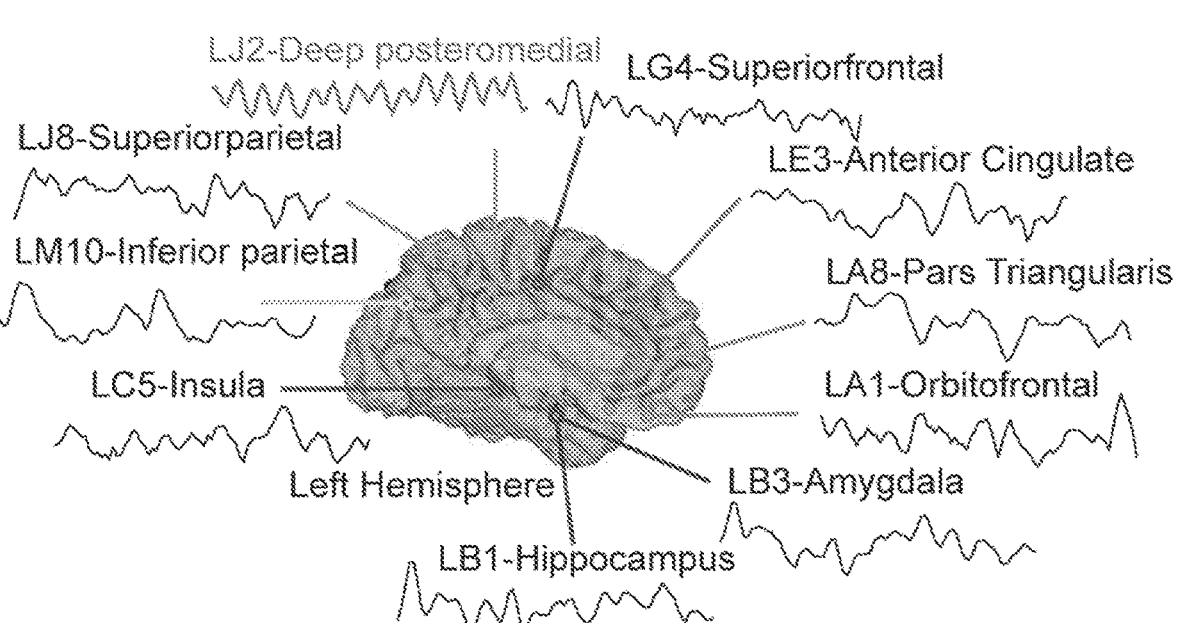

This multi-regional perspective revealed spatially-localized dynamics but did not enable observation of layer-specific cellular contributions. We therefore restricted GCaMP6m expression to specific cortical layers and measured single-neuron RSP $Ca^{2+}$ signals (Extended Data FIGS. 5A 5B). In layer 2/3 neurons (Cux2-CreER mice[16]), neither oscillating neurons nor population synchrony were observed (FIG. 1I, FIGS. 10C, 10D n=5 animals, paired t-test, p=0.7). In contrast, layer 5 neurons (Rbp4-Cre mice[17]) exhibited synchronous activity (FIGS. 1I, 10E, 10F). We verified layer-specificity with brain-wide activity-mapping using the TRAP2 mouse line[18,19]; layer 5 was specifically recruited (unpaired t-test, p<0.001) (FIG. 1J, FIGS. 10G-10I). Thus, under these conditions, ketamine elicited rhythmicity selectively in layer 5 RSP neurons.

Synchronized Spiking in Deep RSP and Subcortical Brain Areas

Figure 2A:
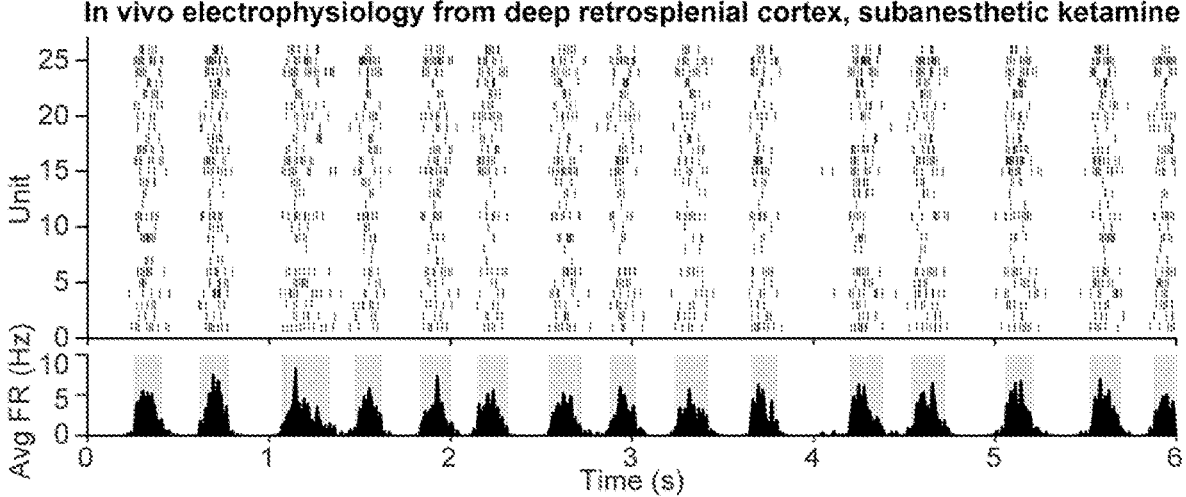
FIGS. 2A-2G. Retrosplenial in vivo electrophysiology.

We extended these findings to the single-spike millisecond-scale domain, electrophysiologically recording with 32-channel two-shank silicon probes. In 50 mg/kg ketamine-injected animals, deep RSP neurons engaged in intermittent ~250 ms synchronous bursts, separated by ~250 ms silent states (FIG. 2A, FIGS. 10J, 10K). Individual units fired ~5-10 spikes/burst; nearly all identified units participated in every burst event, and most bursts contained nearly all units, with structured temporal ordering (FIGS. 10L-10P).

Figure 2B:
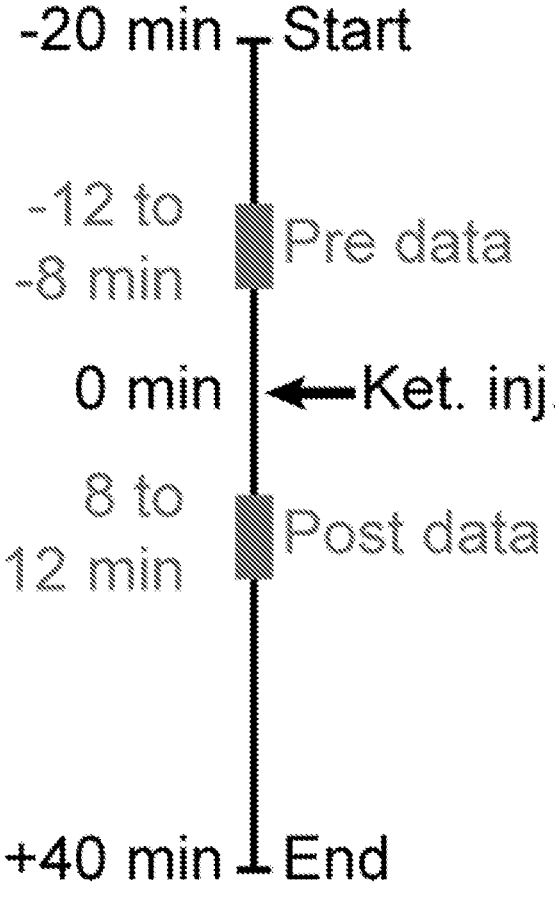
Figure 2C:
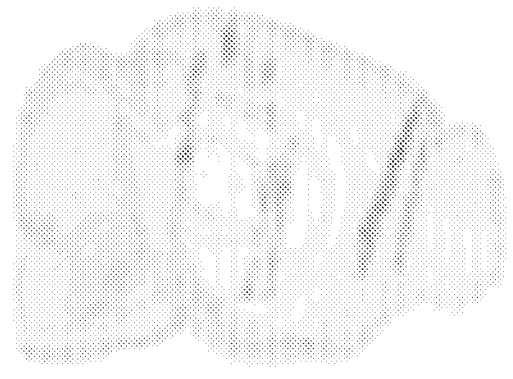
Figure 2C:
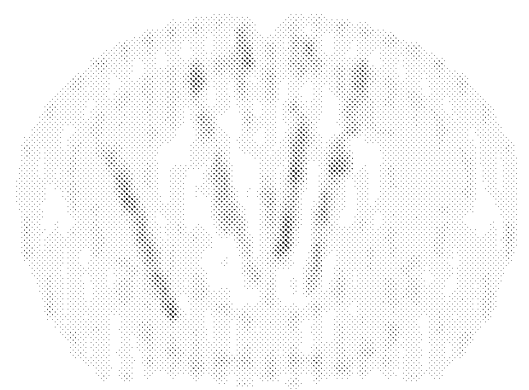
Figure 2D:
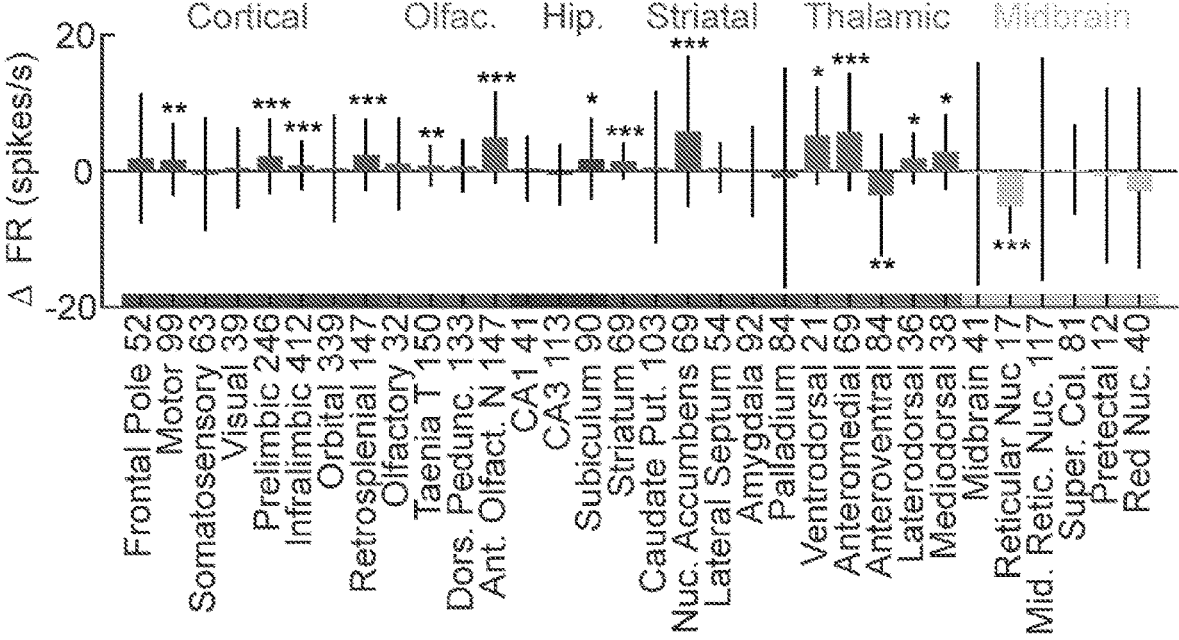
Figure 2E:
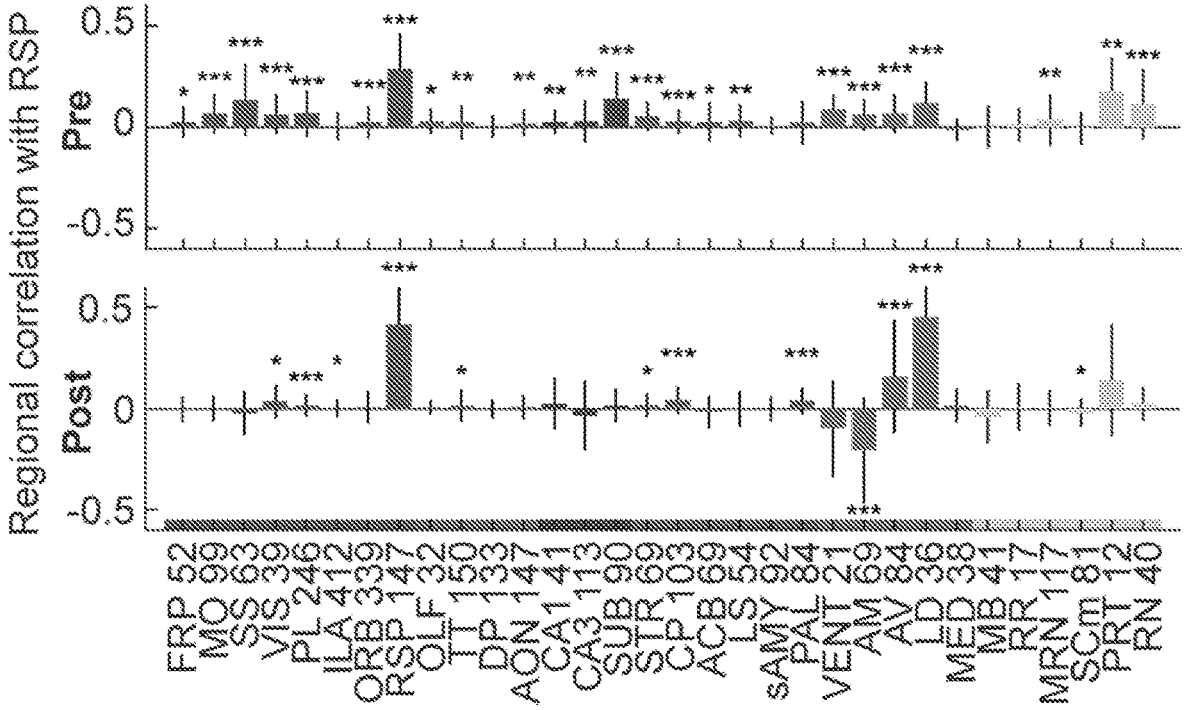
Figure 2F:
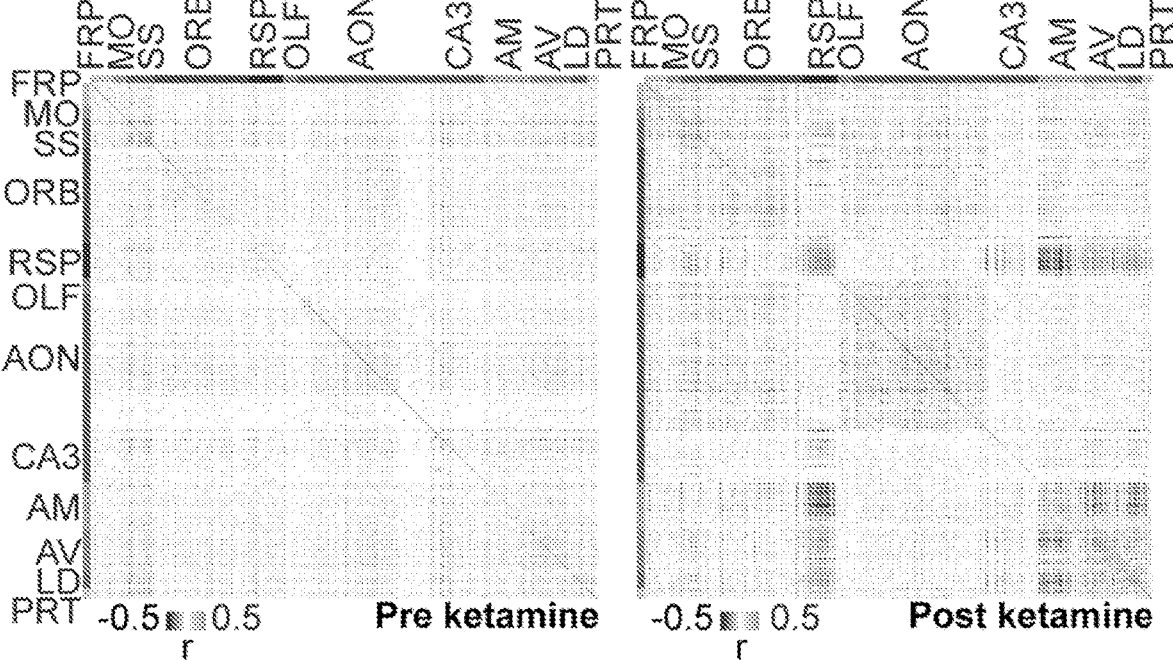
Figure 2G:
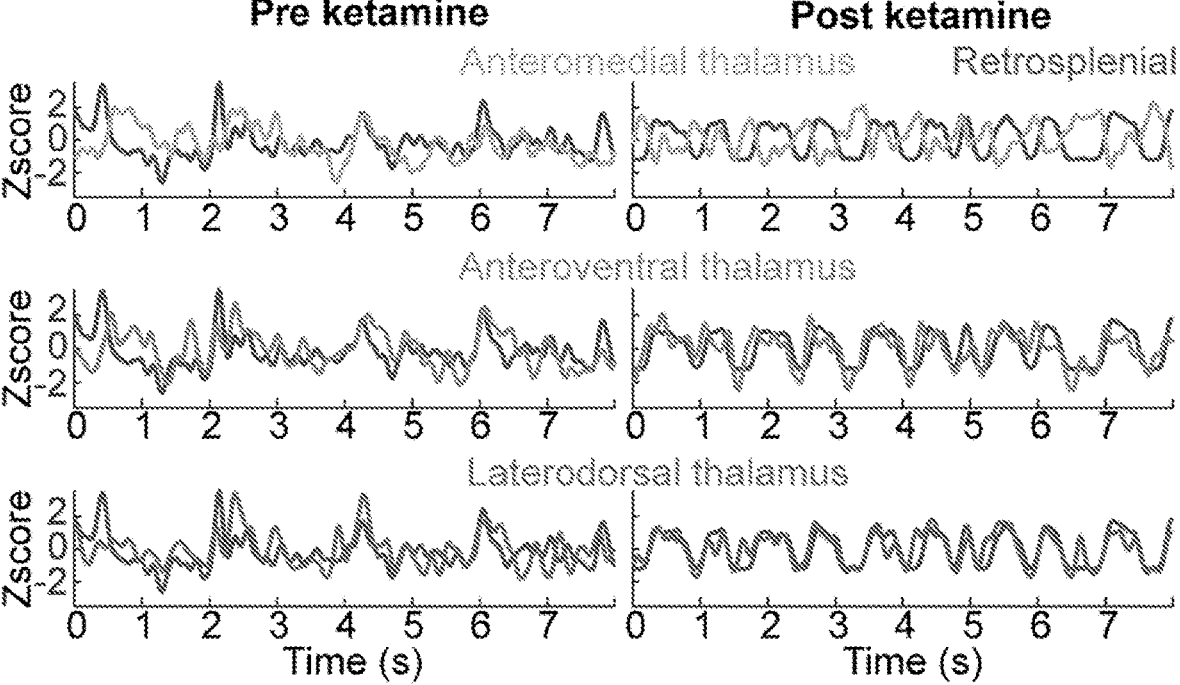

We constructed a four-probe long-shank high-contact-density Neuropixels recording system to simultaneously record hundreds of neurons throughout the brain (FIGS. 2B, 2C, FIG. 11A). Subanesthetic ketamine influenced several brain regions (FIG. 2D, FIGS. 11B, 11C). As expected, we observed the 1-3 Hz RSP rhythm-but also discovered specific subcortical regions (inaccessible to cortical imaging) exhibiting increased rhythmicity (FIGS. 11D-11G). Whereas pre-ketamine nearly-all brain regions were correlated with RSP, 8-12 min after ketamine injection correlations with RSP were reduced (notably in somatosensory cortex, subiculum, ventral/anteromedial thalamus, and the red nucleus (FIGS. 2E, 2F, FIGS. 12A-12E, FIG. 13).

A surprising uncoupling was observed between adjacent (but differently-connected) thalamic nuclei. Whereas laterodorsal and anteroventral thalamus (with known posterior cortical wiring relationships including to RSP[20-22]) became more-strongly correlated to each other and RSP, anteromedial thalamic neurons (with known projections to frontal cortex[20-22]) were found to oscillate out-of-phase with RSP (FIGS. 2F, 2G, FIGS. 12F-121). Thus, brain-wide electrophysiology under subanesthetic ketamine revealed a globally-detectable disconnection motif, interpretable via the rhythm and wiring of RSP.

Dissociative-Like Behavioral Effects Tracking RSP Rhythm

Figure 3A:
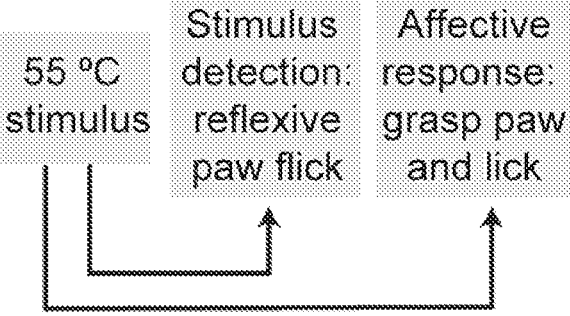
Figure 3B:
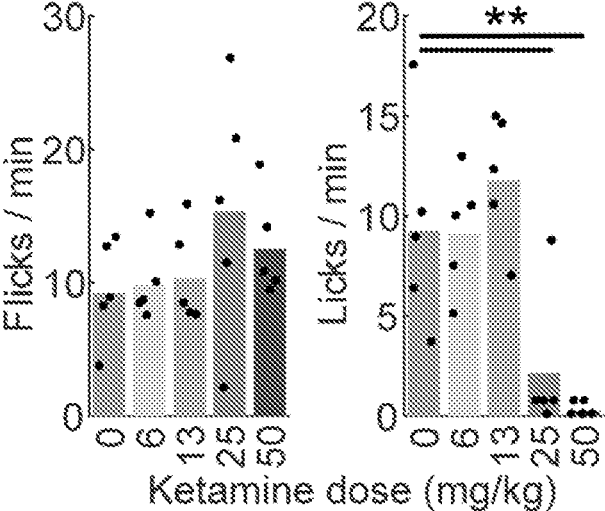

Mice were behaviorally-tested extensively, beginning with reflexive (paw-flick), affective/self-protective (paw-licking) and motivational (jump-to-escape) responses to aversive stimuli (hot-plate test; FIG. 3A). While ketamine did not reduce reflexive responses (paw-flick, one-way ANOVA, $F_{4,20}=1.11$, p=0.38), revealing robustly-preserved sensory-detection and motor capabilities, ketamine abolished affective/emotional (paw-lick, one-way ANOVA $F_{4,20}=10.1$, p<5E-4) and motivational (jump-to-escape, one-way ANOVA $F_{4,20}=105$, p<1E-12) defensive behaviors at 25 and 50 mg/kg (FIG. 3B, FIG. 14A), with similar effects on rearing and behavioral-latency (FIGS. 14B, 14C).

This separability of stimulus-detection from affective-response suggested a dissociation-like state. We next explored longer-timescale escape and social interactions. Ketamine >=25 mg/kg similarly suppressed tail-suspension escape responses (one-way ANOVA, $F_{4,20}=9.36$, p=0.0002) and resident-intruder interactions (one-way ANOVA, $F_{4,15}=13.6$, p<0.0001) (FIG. 14d,e); consciousness was maintained as mice ambulated spontaneously and responded to external stimuli, and the righting-reflex test for consciousness was preserved in all animals (but abolished by anesthetic ketamine; 200 mg/kg, FIG. 14F).

Figure 3C:
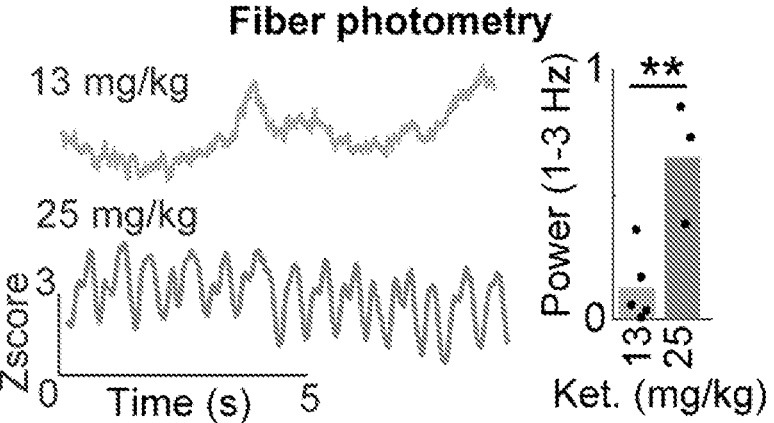
Figure 3D:
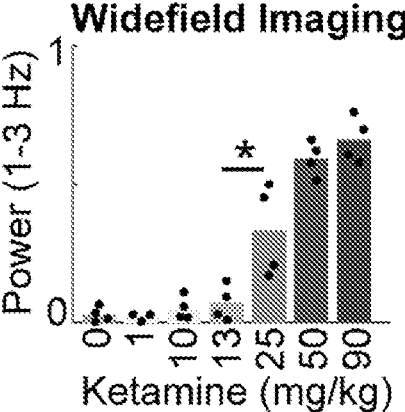
Figure 3E:
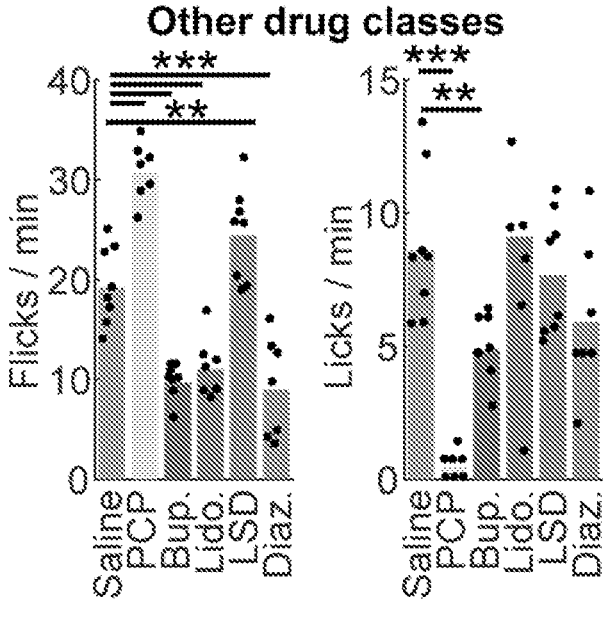

Affective behaviors were consistently preserved at 13 mg/kg, yet selectively abolished at 25 mg/kg. We therefore directly compared RSP activity between these two doses using both widefield imaging, and fiber photometry with locally-expressed GCaMP6m for increased specificity. RSP recordings revealed a 1-3 Hz oscillation at 25 mg/kg—but not 13 mg/kg-suggesting that the 1-3 Hz RSP rhythm could be critical for dissociation-like behavioral effects (FIGS. 3C, 3D).

Figure 3F:
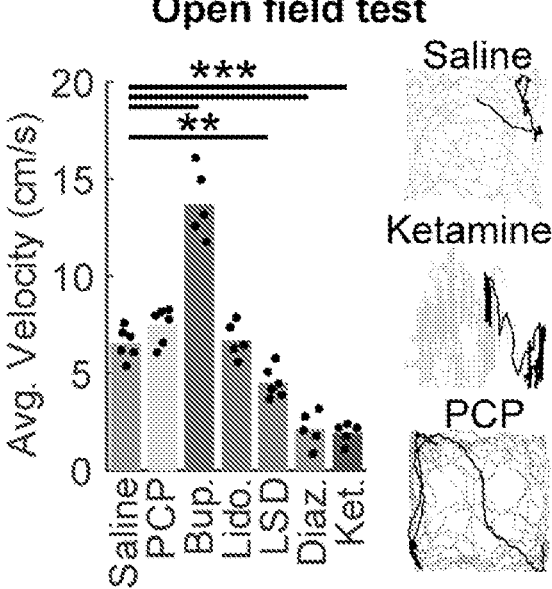

At dissociative doses, ketamine can also induce analgesia, hallucinations, and sedation; we therefore repeated the behavioral panel with four additional classes of drugs that elicit subsets of these effects. The non-sedative dissociative agent PCP alone recapitulated ketamine's behavioral disconnection between sensory-detection and affective responses in the hot-plate test; like ketamine, PCP also inhibited longer-timescale escape and social behaviors (FIG. 3E, FIG. 14G-14K); locomotion velocity was unchanged (FIG. 3F, FIG. 14L). Analgesics (centrally-acting buprenorphine and topical lidocaine) decreased stimulus-detection foot-flicks; neither diminished escape responses (FIG. 14L). The hallucinogen LSD disrupted neither sensory-detection nor affective responses, and tended to increase responsivity to salient stimuli (decreased time-to-jump, increased rearing/socialization) while also reducing locomotion in the stimulus-poor open-field. Finally, the sedative diazepam did not recapitulate dissociative-like behavior.

Together, these results revealed a measurable and consistent dissociation-like behavioral phenotype in mice specifically elicited by dissociative agents (preserved stimulus-detection with diminished affective response) at doses corresponding to emergence of the RSP rhythm.

Rhythmic Drive of RSP Layer 5 Neurons: Elicitation of Dissociation-Like Effects

To test causal impact of this oscillation, we optogenetically delivered the corresponding activity to RSP layer 5 neurons by co-expressing eNpHR3.0/ChR2 (eNPAC) in layer 5 (Rpb4+) RSP and rhythmically-stimulating at 2 Hz (250 ms/20 Hz blue light, alternating with 250 ms continuous yellow light) (FIG. 3G, FIG. 15A). Controls included non-opsin-expressing animals and non-rhythmic (random) illumination of opsin-expressing animals.

While rhythmic RSP drive did not disrupt reflexive responses, affective paw-licking was reduced vs. control (unpaired t-test, corrected p=0.03) (FIG. 3G). Rhythmic drive lengthened time-to-escape vs. non-opsin (unpaired t-test, corrected p=0.02) and random/non-rhythmically-illuminated animals (unpaired t-test, corrected p=0.05) (FIG. 15B), and rearing was reduced in rhythmically-illuminated animals vs. control (unpaired t-test, corrected p=0.02). Rhythmic illumination significantly diminished tail-suspension escape behavior (for which repeated within-animal testing was possible) compared with random illumination in eNPAC-expressing animals (paired t-test, rhythmic vs. random, p=0.01) (FIG. 15E). Rhythmic drive did not reduce resident-intruder social interactions (paired t-test, rhythmic vs. random, p=0.14; Extended Data 10F); righting-reflex and open-field behaviors were unaffected. To test rhythmic optogenetic drive of a different cortical area, we expressed eNPAC in deep layers of somatosensory cortex; here, rhythmic illumination did not induce the dissociative behavioral state (FIG. 3G, FIGS. 15L-15O). In summary, optogenetically providing the activity pattern naturally arising in layer 5 RSP neurons in response to ketamine exerted the effect of dissociating sensory and affective responses.

Physiological and Behavioral Effects of Ketamine Require RSP Rhythm-Generator

Figure 4A:
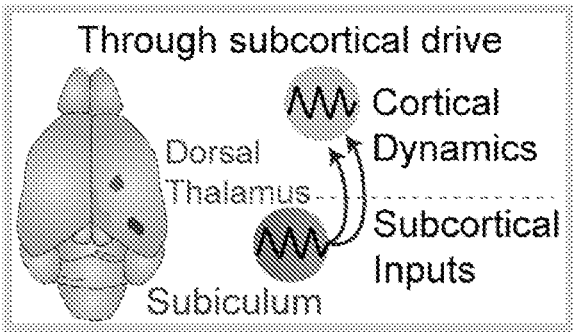
FIGS. 4A-4F. RSP HCN1 channels required for ketamine induction of deep rhythm and dissociation-like behavior.
Figure 4A:
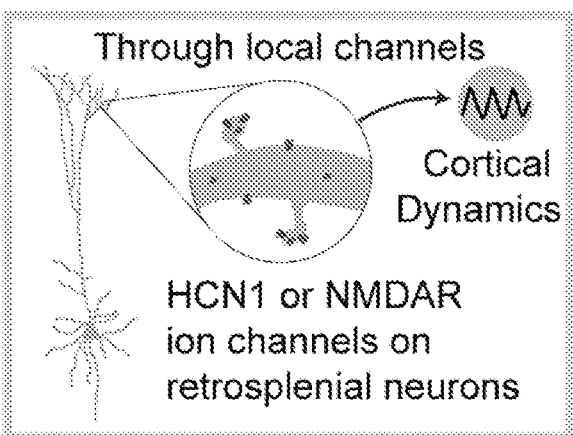

How could systemic ketamine evoke such a layer-specific, focal, and behaviorally-potent rhythm? We explored two major hypotheses: (1) long-range subcortical inputs provided a specific oscillatory drive to layer-5 retrosplenial neurons; or (2) selective expression of specific ion channels in retrosplenial cortex facilitated local oscillations (FIG. 4A).

Figure 4B:
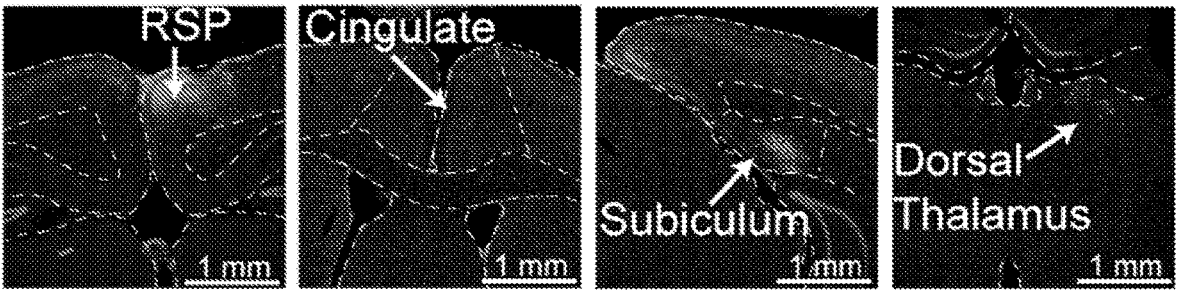
Figure 4C:
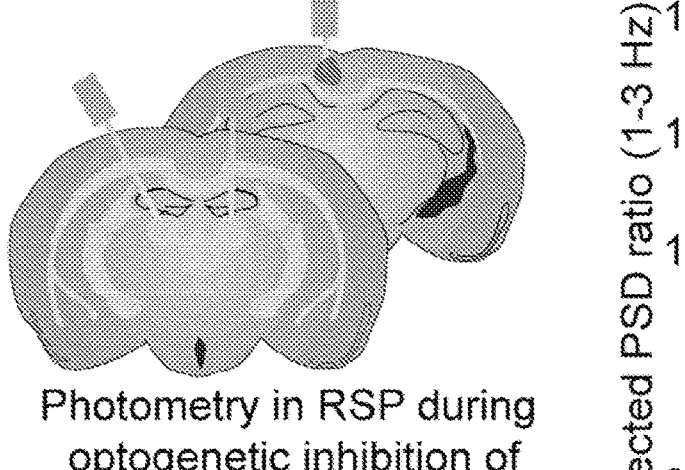
Figure 4C:
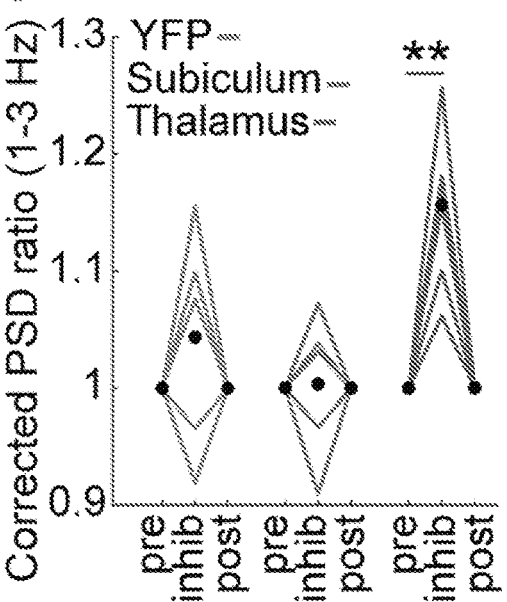

Since thalamic nuclei have been implicated in rhythmicity[23-26], and exhibited oscillations in our electrophysiology, thalamo-cortical loops might contribute to RSP rhythms. To test this hypothesis, we optogenetically inhibited monosynaptic-excitatory inputs (dorsal-thalamus or subiculum) while recording RSP activity after ketamine injection (FIGS. 4B, 4C, FIG. 16a,b). Inhibition of dorsal thalamus did not attenuate, but rather enhanced, the cortical oscillation (paired t-test, corrected p=0.003) (FIG. 4C, FIG. 16C); inhibition of subiculum (or illumination of control animals) had no effect.

Figure 4D:
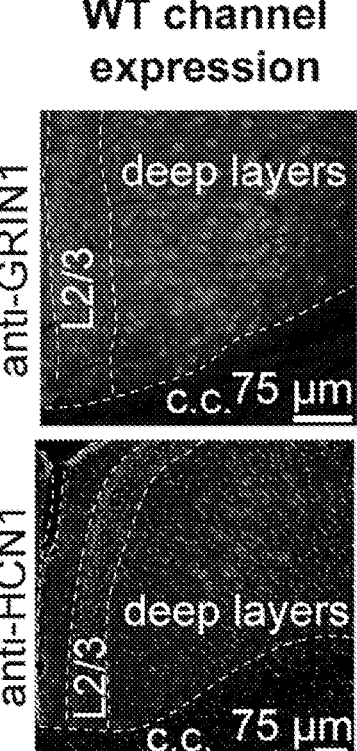
Figure 4E:
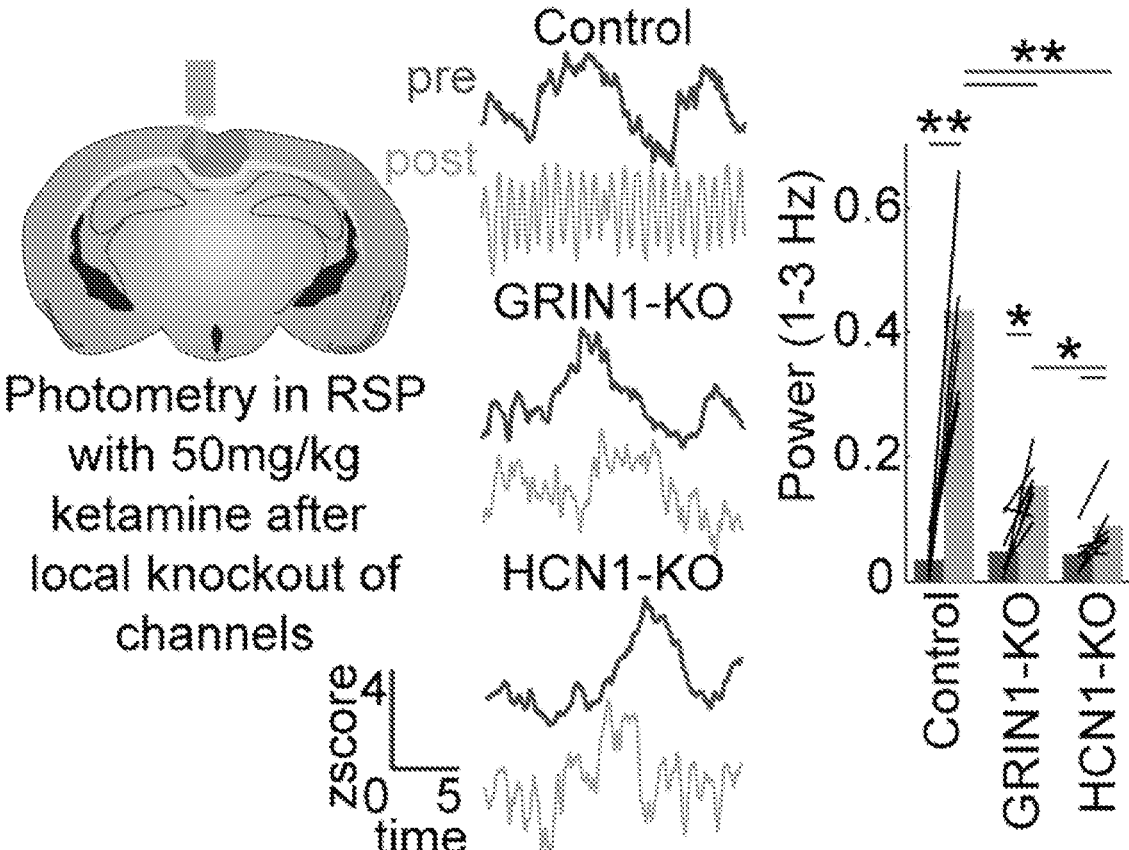

To test local rhythm-generators, we investigated two candidate channels: NMDA-receptors (a primary target of ketamine[27,28] and PCP) and HCN1 pacemaker channels (involved in spontaneous rhythmic firing[29,30]). Immunohistochemistry of HCN1 channels, but not NMDA receptors, revealed high expression localized to deep RSP (relative to layer 2/3 RSP and neighboring deep visual cortex; FIG. 4D, FIGS. 16D, 16I). We recorded from RSP after NMDAR (GRIN1) or HCN1 channels were genetically-disrupted via local injection of AAVdj-Ef1a-Cre and AAVdj-Ef1a-DIO-GCaMP6m viruses into RSP of adult homozygous floxed-channel transgenics, such that GCaMP6m would only be expressed in Cre-expressing and gene-knockout cells (FIG. 4E, FIGS. 15E-15F). After four weeks, ketamine-induced oscillations were significantly diminished in HCN1 and GRIN1 mice, but preserved in wild-type (FIG. 4E, FIG. 16G). By leveraging local-knockout mice, we could thus induce a brain state in which all aspects of global ketamine action would be preserved except for those depending on channels in retrosplenial cortex (without directly inhibiting or lesioning RSP-thus permitting, for example, non-oscillatory RSP activity).

Figure 4F:
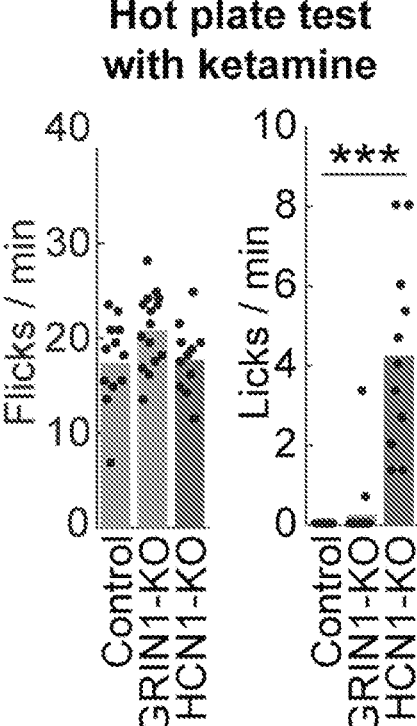

For behavioral experiments, mice were multiply-injected across RSP, yielding local reduction in protein expression (FIGS. 16H-16J). In controls, 50 mg/kg ketamine abolished affective paw-licking while preserving reflexive paw-flicks—the dissociative phenotype (FIG. 4F). RSP injection of Cre-virus in HCN1-KO mice strikingly restored affective paw-licking (Mann-Whitney U, corrected p<0.001); thus, ketamine-imposition of dissociation-like behavior was blocked. Both channel-knockouts also showed modestly-recovered tail suspension-escape behavior (p<0.001) and resident-intruder social interactions (p<0.01) vs. wild-type; all mice successfully-righted postural inversion (FIGS. 16K-16N). Without ketamine, AAVdj-Ef1a-Cre-injected HCN1-KO and GRIN1-KO animals exhibited reflexive and affective behaviors comparable to wild-type C57BL/6 mice (FIGS. 15P-15S). Thus, local RSP HCN1 pacemakers were required for systemic ketamine to induce the deep RSP rhythm and elicit the dissociation-like behavioral state.

Figure 5D:
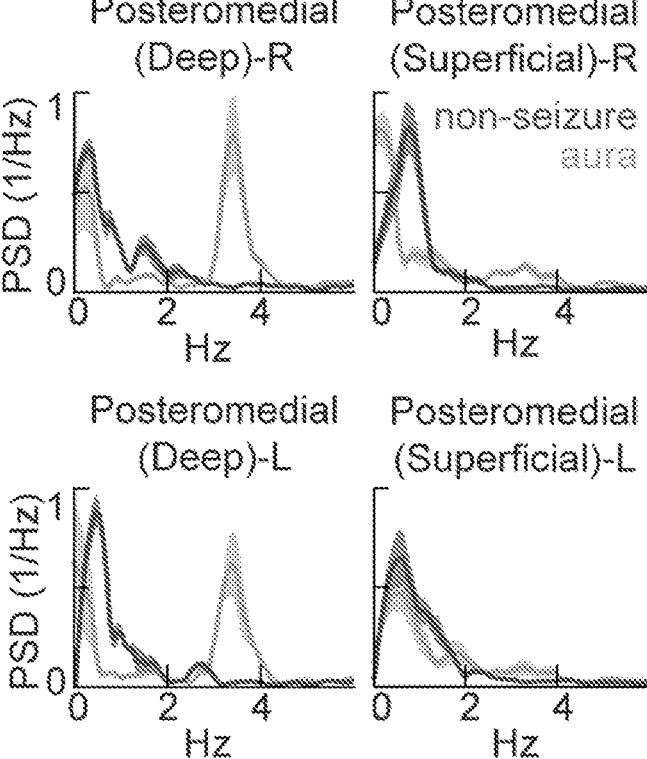
Figure 5E:
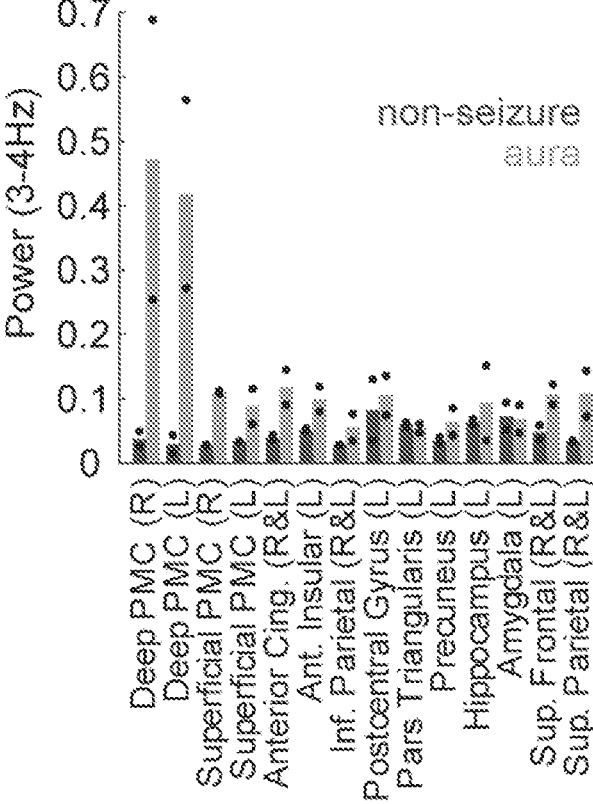

Focal 3 Hz Rhythm in Human Deep Posteromedial Cortex Linked to Self-Reported Dissociation An epilepsy patient at the Stanford Comprehensive Epilepsy Center (with pre-seizure auras described as dissociative) had been previously implanted with brain-wide intracranial electrodes (stereoelectroencephalography) for diagnostic recording/stimulation. Epileptologist inspection of sEEG traces near seizure-onset with dissociative aura revealed a prominent rhythmic waveform only in deep posteromedial cortex (PMC; defined as retrosplenial, posterior cingulate, and medio-ventral precuneus cortex; rodent RSP is considered the closest analog to human PMC areas[31]) (FIGS. 5A-5C; FIGS. 12A, 12B; FIG. 18). Applying the same analyses from mouse imaging, we discovered a sharp oscillatory profile centered on 3.4 Hz restricted to deep PMC (FIGS. 5D, 5E, FIG. 17C). Although the seizure focus was localized to the right hemisphere, left PMC engaged in simultaneous oscillatory dynamics, giving rise to bilaterality as in mouse.

As part of clinical mapping, brief stimulation (50 Hz, 2-10 mA, total duration 1.3+/−0.47 seconds; mean+/−s.e.m.) was applied at individual electrodes. To quantify the elicited response from each stimulation in unbiased fashion, we identified every electrical contact that exhibited rhythmicity during spontaneous dissociative auras (FIG. 17D). Stimulation of the seizure focus in right PMC elicited dissociative, aura-like feelings similar to seizure onset (FIG. 5F). Stimulation of left PMC elicited immediate and confidently-reported dissociative experiences without the negative valence of an impending seizure (comments 4-6). Stimulations through these spontaneously-oscillating PMC contact sites evoked a dissociative aura 11/13 times, whereas virtually no non-oscillating contacts responded in this way (FIG.

5F, FIG. 17E). Only one sham stimulation elicited report of an aura; this one report followed a real stimulation that had elicited a strong aura. Together, these results demonstrated causal elicitation of human dissociative symptoms local to sites exhibiting the deep PMC rhythm.

DISCUSSION

Here, large-scale optical recording technology enabled discovery of a dissociative agent-elicited, layer 5-restricted, low-frequency rhythm localized to deep RSP. This rhythm was associated with elicitation of a dissociation-like behavioral state in mice, and precisely-paced optogenetic intervention revealed that the rhythmic activity itself was causally linked to the dissociative-like effects. RSP-localized knockout of HCN1 channels abolished both the pharmacologically-induced rhythm and dissociation-related behavior. Conscious experience of human dissociation was linked to endogenous rhythmic activity in the homologous deep PMC. These experiments identified molecular, cellular, and physiological properties of a deep posteromedial cortical rhythm underlying dissociation-like states.

Key aspects of dissociation were recapitulated by three specific interventions: administration of retrosplenial rhythm-inducing doses of ketamine or PCP in mice, rhythmic RSP-localized optogenetic stimulation in mice, and similarly-localized electrical stimulation in a patient with epilepsy originating from right PMC (FIG. 19). We note that high-frequency electrical stimulation of non-epileptic PMC (spanning superficial and deep regions across many human subjects, in the absence of the epileptic tissue-dependent low-frequency rhythm observed here) does not induce dissociation[32], consistent with our result that low-frequency rhythmic optogenetic drive was specifically and causally linked to dissociative-like behavioral effects. High-frequency electrical intervention, when delivered to epileptic tissue with specific wiring or ion channel-expression properties, could cause dissociation by several possible cellular mechanisms (including induced rhythmic activity). Likewise ketamine may induce additional effects in human beings beyond RSP rhythm that contribute to its behavioral properties[33-35].

Biophysical mechanisms of both the rhythm and the behavioral state were addressable in the mouse. HCN1 channels underlie $I_h$, a hyperpolarization-activated depolarizing current that can pace rhythmic activity; we found that RSP-specific HCN1 disruption selectively abolished both the ketamine-induced rhythm and dissociation-like behavioral effects. Ketamine blockade of specific depolarizing channels (such as NMDARs) could allow RSP membrane potentials to hyperpolarize, activating intrinsic HCN1 channels and permitting rhythmic dynamics. Our unexpected observations regarding optogenetic inhibition of long-range inputs to RSP, which enhanced (rather than suppressed) ketamine-induced oscillations, were consistent with this model for HCN1 function in posteromedial cortical rhythmicity, as the long-range inputs are likely glutamatergic and excitatory. Cells with certain high HCN1 expression levels may be most susceptible to this effect, a prediction consistent at the regional level with the spatial pattern of cortical HCN1-expression observed and our TRAP2 activity-localization results. The reliable temporal ordering of single-unit spike sequence during each oscillation cycle observed from electrophysiology might reflect the impact of such specific ion channel-expression on membrane dynamics at the single-cell level; future work in humans will be important for probing further how specific differential expression of rhythm-generating channels may contribute to subjective disorders of dissociation. In GRIN1 knockouts, effects were less dramatic than for HCN1 knockouts, and the rhythm's magnitude was partially attenuated without recovery of affective behavior; remaining oscillatory dynamics could be of sufficient potency to cause dissociation, or alternatively the rhythm-attenuated brain state would be permissive for affective behavior expression if postsynaptic temporal integration via functional NMDA receptors were intact.

Regarding functional importance of the ketamine-elicited thalamic oscillation pattern, it is intriguing to consider that the de-coupling of 'primary' thalamic systems (LD, AV; known to connect robustly with posterior forebrain circuitry) and 'secondary' thalamic systems (including AM, projecting to frontal circuitry) could contribute to dissociative symptoms. The inverse correlation of AM from AV, LD, and RSP could affect autobiographical cognition and egocentricity by disconnecting frontal cortical areas from posterior areas, while the 1-4 Hz rhythmicity could maintain continuity of neural activity for >200 ms in each subnetwork to preserve conscious mental experience (distinguishably from anesthesia).

Of all the neocortical regions observed, only PMC exhibited rhythmic activity linked to both dissociative pharmacology and dissociative aura. Interestingly, prior work had suggested that effects of NMDAR-antagonizing agents could be greatest in RSP or PMC[36,37], but the capability for independent functional operation of this cortical region (as revealed here) was surprising in light of data from many laboratories pointing to extensive cortico-cortical wiring and dynamics that integrate neocortex into a distributed network. Such findings largely come from task-performing animals, while human imaging data report PMC to be less active in externally-oriented tasks and more active during stimulus-independent thought, autobiographical cognition, and mind wandering-all self-oriented, task-independent psychological states[38,39].

Future clinical work may include exploring whether electrically-induced low-frequency rhythms in healthy human deep PMC can cause dissociative states, and whether dissociative drugs (or dissociation-linked neuropsychiatric states including PTSD and borderline personality disorder) involve these rhythms in humans. Dissociation in human beings is a self-reported state of mind, and no experimental technique in rodents or humans can currently define in full this subjective experience. However, the clinically-guided paradigm reported here may provide a framework of behavioral, optical, and physiological tools enabling exploration of neural activity underlying dissociative states. These results highlight the value of new brain-scale recording technologies; here, initial optical and electrical multiregional activity-screening guided further quantitative testing of precise causal hypotheses. More generally, integrative technologies with broad and high-resolution perspective may provide increasingly-informative experimental access to internal representations of sensations, cognitions, and actions at cellular resolution (and with region-wide or even brain-wide perspective), providing a path forward for elucidating the dynamics involved in creating complex brain and behavioral states important in health and disease.

Methods

Experimental Model and Subject Details

All procedures were in accordance with protocols approved by the Stanford University Institutional Animal Care and Use Committee (IACUC) and guidelines of the National Institutes of Health. Mouse strains used were C57BL/6J (Black 6, Jackson Laboratory, #664), Tg(Thy1-GCaMP6s)GP4.3Dkim (Thy1-GCaMP6s, JAX #024275), Cux2-CreERT2 (gift of S. Franco, University of Colorado), Ai148(TIT2L-GC6f-ICL-tTA2)-D (Ai148, Jax #030328) (gift of H. Zeng, Allen Institute for Brain Science), Tg(Rbp4-cre)KL100Gsat (Rbp4-Cre, No. 031125-UCD, MMRRC) (gift of L. Luo, Stanford), B6.129S-Hcn1tm1KndI/J (HCN1$^{f/f}$ Jax #028299) (gift of L. Giocomo, Stanford), B6.129S4-Grin1tm2Stl/J (NR1$^{f/f}$ Jax #005246). Male and female mice were used, aged 6-24 weeks at the time of surgery. Mice were group housed in plastic cages with disposable bedding on a standard light cycle until surgery and behavior, when they were moved to a 12 hr reversed light cycle.

Drug Administration

Drugs used were ketamine (VEDCO, ketamine HC1, 6-200 mg/kg), phencyclidine (PCP, 5 mg/kg, Sigma-Aldrich P3029), memantine (50 mg/kg), MK801 (0.75-1 mg/kg), dexmedetomidine (0.35-1.5 mg/kg), propofol (35-140 mg/kg), xylazine (AnaSed AKORN, 12.5 mg/kg), buprenorphine SR (2 mg/kg), lidocaine (topical), LSD ((+)-Lysergic acid diethylamide (+)-tartrate (2:1), 0.3 mg/kg), and diazepam (2 mg/kg). For all imaging, recording, and behavioral experiments, drugs were injected intraperitoneally (with a 26-gauge needle) 10 minutes before data was taken unless noted otherwise (e.g. see ketamine injection for Neuropixels experiment). For injection during imaging or Neuropixels recording, a catheter was implanted intraperitoneally before head-fixation (BD Saf-T-Intima #383323). For anti-depressant effects, human doses are typically 0.3-1 mg/kg, and in mouse 3-10 mg/kg. Following the same pattern, humans consistently report potent dissociation at ~2-3 mg/kg, and in the mouse, the lowest tested dose causing the oscillation and behavioral effects was 25 mg/kg[40-42]. Thus, the dose-response relationship for dissociative effects of ketamine in mice corresponds with human/mouse mapping for previously-studied effects of ketamine.

Pan-Cortical Imaging with Blood Autofluorescence Correction

As described[8], mice were anesthetized with isoflurane, the scalp was removed, the skull cleaned and dried, and a custom head-plate was cemented to contacts over the cerebellum and in front of the olfactory bulb. The skull was then covered in a thin layer of cyanoacrylate glue (Apollo 2000, Cyberbond), clear dental acrylic (Ortho-Jet, Lang Dental), and clear nail polish (Electron Microscopy Services). Buprenorphine SR (0.1 mg/kg) was injected subcutaneously for pain management. Mice were given >=1 wk recovery before experiments. Imaging was performed on a custom-built fluorescence microscope designed for high light collection efficiency and large field of view. The microscope consisted of back-to-back 50 mm f/1.2 camera lenses (Nikon), separated by a FF495-Di03-50.8-D dichroic mirror (Semrock), mounted in a 60 mm cube (Thorlabs). An F-mounted ORCA Flash 4.0 (Hamamatsu) was used to record images, with a FF01-520/35-50.8-D emission filter (Semrock). Alternating 410 nm and 488 nm illumination for non-Ca$^{2+}$ dependent artifact removal was controlled using a microcontroller (Arduino) slaved to the frame output trigger of the camera.

Two-Photon Imaging

Mice were anesthetized with isoflurane and the skull above retrosplenial cortex was removed and replaced with a 7 mm circular glass coverslip. For layer 1 experiments, Thy1GcaMP6s mice were used. For layer 2/3 experiments, Cux2-CreER; Ai148 mice were used (tamoxifen dissolved in corn oil was injected intraperitoneally at 0.1 mg/g at least 2 weeks prior to imaging). For layer 5 experiments, Rbp4-Cre mice were injected locally in retrosplenial with 800 nL AAVdj-Ef1a-DIO-GCaMP6f (titer 5E12) at stereotactic coordinates (−3AP, 0.5ML, −0.6DV). Mice were given >=1 week to recover before imaging. Awake, head-fixed imaging was performed on a standard two photon microscope (NeuroLabWare, Los Angeles, CA). A 16x 0.8 NA Nikon objective was immersed in clear ultrasound gel for imaging (Aquasonic, Parker Laboratories); frame rate of 30 Hz. Although we observed oscillations in RSP with 50 mg/kg, we were concerned that 50 mg/kg may be too low a dose to sensitively detect a potentially weaker signal in visual cortex or layer 2/3, and so we used 80 mg/kg in these experiments.

Ketamine-TRAP Experiments

Dissolved 4-OHT (20 mg/mL in ethanol) was mixed with corn oil at a concentration of 10 mg/mL, and ethanol evaporated by vacuum centrifugation (60 minutes). Mice were each placed alone in a novel cage for 30 minutes, to remain for the experiment. Two mice were injected with 50 mg/kg ketamine intraperitoneally, and two mice were injected with an equivalent volume of saline. After 1 hr, all mice were injected with 50 mg/kg tamoxifen, as well as an additional dose of 50 mg/kg ketamine/saline. After 1 hr, a final dose of ketamine/saline was administered. This protocol was designed to ensure that the ketamine-induced oscillation (and associated cFos expression) was occurring throughout the majority of the ~4 hr post-tamoxifen-injection time window during which TRAP2 labels cells. After 10 days (to allow time for expression of tdTomato), mice were perfused with ice cold PBS and 4% PFA. Coronal sections (50 μm) were taken using a vibratome and imaged on an epifluorescence microscope.

In Vivo Electrophysiology

Retrosplenial Targeted Recordings

Mice were anesthetized with isoflurane, a small craniotomy (~2 mm diameter) was performed above retrosplenial cortex, and a custom head-plate implanted. The dura was gently removed, and then covered with Kwik-Cast Sealant (World Precision Instruments). A skull screw was implanted and secured with cement in the right frontal skull bone. Mice were given 1-2 hours to recover. Next, mice were i.p. injected with 50 mg/kg ketamine, and head-fixed under an in vivo electrophysiology recording apparatus. To record neural activity, a 32-channel two-shank silicon neural probe (ASSY-37 P-1, Cambridge NeuroTech) was slowly lowered into retrosplenial cortex. The deepest tip of the electrode was 800-1000 μm from the brain surface for all recordings.

Simultaneous Recording from Four Neuropixels Probes with i.p. Drug Delivery

Surgeries

Mice were anesthetized with isoflurane, carefully leveled in a stereotaxic apparatus and their scalp and periosteum were removed. A 3% hydrogen peroxide in saline solution was used to clean the surface of the skull. A custom stainless steel headbar was leveled on the skull and attached using clear dental cement. After the cement had dried, targeted probe entry sites were stereotaxically marked on the cement layer with a permanent marker (Day 1: "mPFC", 2.3AP, 0.6ML; "somatosensory", −0.7AP, −4.0ML; "retrosplenial", −2AP, −1 ML; "subiculum", −3.5AP, 2.14ML; Day 2: "OFC": 2.5AP, 1.5ML; "mPFC": 2.3AP, −0.6ML; "retrosplenial", −2AP, 1ML; "thalamus", −1.5AP, −1.7ML). In part, they were selected to cover areas with known connectivity to the retrosplenial cortex. A 2 mm long insulated platinum-iridium wire was implanted centrally over the cerebellum, with the last several hundred microns bared to serve as an electrical reference. Buprenorphine SR was administered to relieve pain and mice were allowed to recover for at least one week before recordings began.

Electrophysiological Recording

Mice were acclimated to head fixation and the recording rig over several days before recording. Several hours before recording, mice were anesthetized for approximately 30 minutes each while small 1 mm craniotomies were made over four pre-marked areas. Craniotomies were kept clean of bone fragments and made such that bleeding was minimized. The skull was covered with a pool of saline and with Quik-Cast to protect and keep moist craniotomies before recording. Mice recovered in their homecages before recording. Immediately prior to recording set up, mice were very briefly anesthetized with isoflurane and implanted with an IV catheter system (BD Saf-T-Intima Closed IV Catheter System: 22G×3/4', containing an integrated Y adaptor and safety lock) to their intraperitoneal cavity and affixed with glue. The microtubing had been previously loaded with a ketamine/saline solution (0.1 ml of 100 mg/ml Ketamine solution (KetaVed, VEDCO) in 2 ml of saline) and was maintained at neutral pressure using a syringe attached at the distal (from the animal) end of the fluid line. While still anesthetized, mice were headfixed and tubing was secured stably to a custom mouse holder by tape. Quik-Cast was removed from the skull, and craniotomies were briefly cleaned before being submerged in a pool of saline. Four Neuropixels 1.0 probes[43,44], were grounded together with the mouse reference electrode, coated with red fixable dye (CM-Dil, ThermoFisher), positioned over each craniotomy, and carefully inserted at approximately 15 degrees from the vertical axis to depths of 4-5 mm at a rate of approximately 3 um/s. Following the completion of all insertions, the probes were allowed to rest for at least 10 minutes before the recording began. 30 kHz data was acquired from the four probes simultaneously using the Neuropixels control system (as described in the User Manual) and SpikeGLX software (billkarsh.github.io/SpikeGLX/). The four acquisitions were synchronized using a common squarewave signal recorded for all probes and aligned to the nearest pulse edge. Following the beginning of recording, a 20-minute baseline period of activity was collected. A 50 mg/kg dose of ketamine was then remotely injected i.p. through the catheter system, the administration time was marked, and an additional 40 minutes of activity were recorded. Following recording, craniotomies were sealed and the skull was covered with Kwik-Cast. A custom MATLAB script wrapping Kilosort2[45] (github.com/MouseLand/Kilosort2) functions was used to spike sort data, using default Kilosort2 parameters. Following spike sorting with Kilosort2, clusters were manually curated in Phy (github.com/cortex-lab/phy) to separate "Noise" clusters from "Good" clusters. Clusters were considered "Noise" if they contained electrical artifacts, were not well isolated, or appeared to drift off of the probe (trend in decreasing amplitude correlated with decreasing spike rate). Subsequent analysis was performed using custom Python code.

Histology

Animals were perfused with phosphate buffered saline (PBS) and 4% paraformaldehyde (PFA) before overnight postfixation in 4% PFA at 4° C. Postfixed brains were maintained for <1 week at 4° C. in PBS until subsequent use. Brains were dehydrated in a methanol gradient and subsequently processed as described previously[46]. Whole brains were imaged with horizontal optical sections on a LaVision light sheet microscope in dibenzyl ether for 488 nm autofluorescence and 532 nm CM-Dil electrode tracts. Image stacks were downsampled to 25 micron resolution and registered using autofluorescence signal to the Allen Brain Atlas CCFv3. Nonlinear registration and transformation was performed using Elastix. Transformed CM-Dil electrode tract data was traced in CCF coordinates using a custom variant of AllenCCF software (github.com/cortex-lab/allenCCF) and subsequently processed using custom Python code for tract reconstruction and location assignment. Well isolated unit locations were assigned to the electrode location with peak unit amplitude. This location was used to label a unit with the nearest reference atlas subdivision. Reconstructed tracts were manually assigned to corresponding Neuropixels probe recordings. As individual probe insertions were distant from each other and labeled by hemisphere on the day of insertion, 8 tracts per brain (from two sessions of recording per mouse) could be unambiguously assigned.

Data Analysis

Following recording time synchronization for all spike times (as described above), spikes for each "Good" unit were binned at 10 ms intervals and smoothed using a 50 ms width causal moving average filter, resulting in a smoothed spike rate. When shown, spiking data is not binned or smoothed. Correlations were computed using smoothed spike rate traces. For correlations with RSP, a single trace was computed with RSP as the mean firing rate across all units in RSP. This RSP trace was then correlated separately with the firing rate of each individual unit from that recording session. Firing rate was computed as the mean smoothed spike rate across the designated four-minute window before or after ketamine administration (either minutes −12 to −8 or +8 to +12). For plotting z-scored traces, for each trace, its mean was subtracted and it was divided by its standard deviation. To select units for showing in raster plot, units were sorted based on their correlation of their smoothed spike rate with the mean smoothed spike rate across all RSP units, and the top five units from each region were shown.

Fiber Photometry

A 405 nm and 470 nm LED illumination (Thorlabs) was combined (425 nm longpass, Thorlabs DMLP425) and coupled into a fiber optic patch cord (400 μm diameter, 0.48 NA, Doric Lenses) using a longpass dichroic (505 nm, Thorlabs DMLP505) and a fixed-focused coupler/collimator with a standard FC connector (F240FC-A, NA 0.51, f=7.9 mm)[47,48]. Each illumination channel was frequency modulated using the sync output from a lock-in amplifier (SR810 DSP, Stanford Research Systems). GCaMP fluorescence was collected through the same patchcord and delivered through a bandpass emission filter (Semrock, FF01-520/35) onto a NewFocus 2151 femtowatt silicon photoreceiver (Newport, DC Low mode). The signal from the photoreceiver was split into each lock-in amplifier, and the filtered outputs were digitized at 5 kHz using a NIDAQ (National Instruments PCIe-6353) and saved using a MATLAB (MathWorks) acquisition script.

Data Processing and Analysis for Recordings

General Statistical Analysis

Sample sizes were chosen using standards in the field established in previous published studies and our lab's experience with the behavioral tests. Mean+/−s.e.m. was used to report statistics unless otherwise indicated. The statistical test used and the definition n for each analysis is listed in the Results text or figure legends. Multiple comparisons were false discovery rate corrected for by Benjamini-Hochberg correction (alpha=0.05) and is indicated in the text as "corrected p=". No statistical methods were used to pre-determine sample size. Criteria for animal exclusion was pre-established: animals were excluded if injected virus did not express or optical fibers were mistargeted. Variances were similar between groups that were statistically compared except in a few cases where the mean and variance near zero. Effect size was calculated using either Hedge's g, or Glass's delta was used if group variances were very different.

Widefield Imaging and Fiber Photometry

Analysis was performed using custom MATLAB (MathWorks) scripts. Widefield imaging videos were registered to a 2D top-projection atlas generated from the annotated Allen Brain Atlas volume, version CCFv2, in MATLAB (MathWorks), using an affine transformation computed from four manually selected control points. Each video was DF/F normalized, using the median for each pixel over the entire time series as F. The 410 nm channel was then temporally smoothed using a moving average (width=400 ms). The smoothed 410 nm DF/F signal for each pixel was regressed onto the 488 nm DF/F signal for the corresponding pixel, and the regression coefficients were used to scale the 410 nm channel to the 488 nm channel. This scaled 410 nm DF/F signal was then subtracted from the 488 nm DF/F signal to produce a normalized signal for each pixel. For quantification, activity traces were extracted from points centered in five cortical regions (visual, somatosensory, parietal, motor, retrosplenial) on the left hemisphere of the brain. The video data was Gaussian smoothed spatially (radius=2 pixels). Similarly, for fiber photometry recordings, the 410 nm signal was regressed onto the 488 nm signal, the 410 nm signal was scaled by the regression coefficients, and then subtracted from the 488 nm signal.

Two Photon Imaging

Two-photon tiff stack videos were registered to the average image using the TurboReg ImageJ plug-in using rigid body transformations. Cellular region of interests (ROIs) were manually selected, since automated algorithms did not perform well in detecting cells with oscillatory activity. Contaminating neuropil signal was estimated from an annulus surrounding each soma mask and removed using the function F(t)=Fsoma(t)-0.3*Fneuropil(t), where Fsoma(t) is the somatic DF/F and Fneuropil(t) is the DF/F from an annulus 4 pixels wide surrounding each soma mask. The resulting traces were detrended and z-scored. The full frame fluorescence (used for quantifying layer 1 neuropil oscillations) was computed by summing all of the pixels in each frame on each time point, and then computing DF/F the same way, with no neuropil subtraction step.

Frequency Analysis

Each trace (corresponding to either a fiber photometry signal, a cellular two-photon signal, a widefield regional centroid, a widefield pixel, an sEEG trace, or a smoothed spike rate Neuropixels trace) was z-scored, and the power spectral density (PSD) was then estimated using Welch's method (pwelch( ) in Matlab), with a window size of 10*fs (15*fs for human sEEG) where fs is the sampling rate of the signal. The average band power within a specified band (i.e. 1-3 Hz) was then computed by integrating the PSD estimate (bandpower in Matlab). For displaying the traces of individual cells, traces were each zscored by subtracting the mean value of the trace (across the whole recorded time window) and dividing by the standard deviation of the trace. Unless otherwise indicated, the PSD was computed across the time window from minutes 10 to 11 post-injection.

Electrophysiology

32-Channel Acute Silicon Probe Recordings

Extracellular electrophysiological data were recorded using 32 channel acute silicon probes (ASSY-37 P-1, Cambridge Neurotech) acquired at 30 kHz. Following common average referencing, well-isolated single units were identi-
fied using KiloSort and Phy. Data were analyzed using
custom Matlab scripts. Instantaneous firing rate was com-
puted using 1 ms bins. We used a Hidden Markov Model
with two states to label ON and OFF states. ON states were
considered to represent bursts, and OFF states were inter-
burst intervals. We fit the emission and transition parameters
of the model using the Baum-Welch algorithm (Matlab
hmmtrain with a convergence threshold of 1e-6 and initial
guesses of transition matrix: [0.95, 0.05; 0.05, 0.95] and
emission: [0.5, 0.5; 0.1, 0.99]), and then estimated the state
assignment at each time point using the Viterbi algorithm
(Matlab hmmviterbi). Various initial guesses were tested,
and they yielded the same or similar model fit. For popula-
tion analyses, a bin size of 2 was used. In FIG. 10, we are
looking at the number of spikes in each burst, which can
vary depending on the neuron being recorded, so we
included every burst for every neuron. To quantify the
consistency of the sequential onset of activation across
bursts, we ranked each unit by its onset time for each burst.
We then ordered the units according to their median rank
across bursts. For each burst, we fit a linear model between
the ranking in that burst and the median rank. The distribu-
tion of correlation coefficients was then plotted across bursts
for each mouse and treatment condition.

Rodent Behavior

General Behavioral Notes: Mice were handled and accli-
mated to patch cord coupling before testing. Opsin and
control mice were randomly distributed across group-
housed experiment cages. Experimenters were blinded to
animal identity during performance and scoring of each
behavioral assay, as well as when assessing viral expression
and fiber placement. For all statistical tests between groups
and involving multiple comparisons, a Benjamini-Hochberg
false discovery rate correction was used.

Hot Plate Test: Mice were placed on the hot plate (Bio-
seb), which was set to 55° C. and surrounded by a clear
circular perimeter. Mouse activity was recorded using two
cameras from different angles. The experiment ended when
the mouse jumped to escape or 90 seconds had elapsed. Care
was taken to clean and dry the hot plate apparatus between
animals. For optogenetic experiments, mice were connected
to patch cords and then returned to a holding cage. Illumi-
nation began 30 seconds before mice were placed on the hot
plate.

Tail Suspension Test: Mouse activity was recorded using
a 60 Hz web camera. Struggling activity was quantified for
minutes 2-10. For ketamine experiments, tail suspension
began 5 minutes after injection, so that post injection min-
utes 7-15 were used for scoring. For optogenetic experi-
ments, mice were connected to patch cords and then returned
to a holding cage. Illumination began 30 seconds before tails
were secured with tape and suspended from the beam. Mice
were excluded if they climbed on their own tails.

Social Interaction Assay: Resident-intruder social inter-
action was recorded for two minutes. Interactions were
defined as close physical proximity behaviors, including
sniffing, touching, and following. For optogenetic experi-
ments, mice were connected to patch cords and then returned
to their home cage. Illumination began 30 seconds before the
same-sex intruder mouse was introduced.

Righting Reflex Assay: Mice were held at the neck and
tail, rotated to supine position on a flat surface, and quickly
released. Time to right was quantified as moment of release
to moment when all 4 legs touched the ground. A five second
threshold was used to classify righting success (less than 5
seconds) from failure (more than 5 seconds). For optogenetic experiments, mice were connected to patch cords and
then returned to a holding cage. Illumination began for 30
seconds, and then the mouse was swiftly inverted onto the
flat surface.

Open Field Test: Mice were placed in an evenly illumi-
nated 50 cm×50 cm open field test box. Mouse position was
captured using a webcam and Viewer software (Biobserve).

Retrosplenial Optogenetics

Stereotaxic Surgery: Adult male and female Rbp4-Cre
transgenic animals were bilaterally injected with either 1 µl
of AAV1-nEF-DIO-eNpHR3.0-p2a-ChR2(H134R)-YFP (ti-
ter 5E12, known as eNPAC 2.0, and referred to in the text
as eNPAC) or AAV5-Ef1a-DIO-eYFP (titer 5E12) in retro-
splenial cortex (AP −3.3, ML+/−0.5, DV 0.5). A fiber was
implanted above each injected area. For S1 opsin-expressing
animals, the injection was made at (AP+0, ML+/−3.0, DV
0.5). Viruses were obtained from the Stanford Neuroscience
Gene Vector and Virus Core. Animals were given four weeks
for viral expression and recovery before experimentation.

Illumination Parameters: For blue light: 473 nm laser, 10
ms pulses, 20 Hz, 20 mW at fiber tip. For yellow light: 594
nm, continuous light, 15 mW at fiber tip. Alternating 250 ms
bouts of pulsed blue light and continuous yellow light were
used for oscillatory stimulation experiments. For non-rhyth-
mic stimulation, alternating 20 Hz blue light and continuous
yellow light were also used but with length of each illumi-
nation randomly selected from a uniform distribution with a
minimum of 50 milliseconds and a maximum of 2 seconds.
Each 30 seconds, blue light and yellow light pulse lengths
were selected such that the total time allotted to blue or
yellow light across 30 seconds matched that of the rhythmic
group.

Subcortical Projection Optogenetics with Fiber Photometry

Stereotaxic Surgery: Adult male and female wildtype
C57/BI6 wild-type animals were bilaterally injected into
dorsal anterior thalamus (AP −1.2, ML+/−1, DV 3.25) or
subiculum (AP −3.8, ML+/−2.5, DV −2.2) with 500 nL of
either AAVdj-CaMKIIa-NpHR3.0 (titer 5.15E12) or AAV8-
Ef1a-eYFP (titer 5E12). Then, 500 or 600 nL of AAVdj-
CaMKIIa-GCaMP6m was injected in right retrosplenial
cortex (AP −3.3, ML 0.5, DV 0.5). A fiber was implanted
above each injected area (with one of the subcortical fibers
angled at 30 degrees). Four weeks were allowed for viral
expression and recovery before experimentation.

Illumination Parameters: 594 nm, continuous light, 15
mW at each fiber tip. Eight minutes after ketamine (50
mg/kg) administration, six minutes of photometry data were
recorded: two minutes of pre-illumination photometry were
recorded, followed by two minutes with continuous illumi-
nation, and then two minutes of post-stimulation.

Histology: For monosynaptic input tracing, adult male
Rpb4-cre animals were injected with AAV8-EF1a-DIO-
TVA-p2A-oG (9E12) into retrosplenial cortex. Two weeks
later, ENVA-Rabies-GFP (3E8) was injected in the same
location. After five days, animals were perfused, brains fixed
overnight, and sectioned into 50 µm sections; full coronal
sections were imaged on a confocal microscope for cell
counting.

Retrosplenial Gene Disruption and Fiber Photometry

Stereotaxic Surgery: Adult male and female HCN1^{f/f},
NR1^{f/f}, or wildtype C57/BI6 were injected bilaterally in two
retrosplenial locations (AP −3.1 and −3.4, ML+/−0.5, DV
−0.5) with 1 uL of AAV8-Ef1 a-mCherry-IRES-Cre (titer
5E11) and AAVdj-Ef1a-DIO-GCaMP6m (titer 1E13). A
400-micron optical fiber was implanted over one injection
location. At least four weeks were allowed for viral expres-
sion and gene disruption before photometry recording. For gene knockout behavior experiments, injections of AAVdj-Ef1a-Cre were made at (AP −2.7, −3.1 and −3.5, ML+/−0.5, DV −1.35 and −0.70). For gene knockout control behavioral experiments, two retrosplenial injections of AAVdj-Ef1a-Cre were made in experimental animals.

Rodent Histology: After PFA-perfusion and overnight fixation in 4% PFA at 4C, 50 μm sections were taken on a vibratome. For immunohistochemistry, sections were washed in PBST (0.3% Triton-X) for 1 h, blocked with 1% BSA for 30 minutes, and then incubated with primary antibody in 1% PBST-BSA overnight. Primary antibodies used: anti-HCN1: 1:500 of abnova MAB6651 lot MH387188, anti-NMDAR: 1:500 of Invitrogen RA5-85751, lot UF2785857C. Next, sections were washed for 30 min in 1% PBST and then incubated with secondary antibody (1:500 in PBST-BSA) for 90 min at room temperature, and then washed for 1 hour in PBST. Sections were mounted on slides and imaged using a confocal microscope.

Human Intracranial Electroencephalography (sEEG) Recordings

All clinical research was reviewed and approved by the Stanford Institutional Review Board. Informed consent was obtained from the subject prior to participation in the study protocol. The patient (participant number S19-137/SD056) was implanted with Ad-Tech (Oak Creek, WI) SEEG Depth Electrodes as part of routine Phase II monitoring for refractory epilepsy. A 10 kHz research copy of the patient's electrophysiological data was acquired over Ethernet, simultaneous with inpatient clinical recording, via a Nihon Khoden (Tokyo, Japan) JE-120A junction box as part of an EEG-1200 clinical acquisition system. For ease of processing, the 10 kHz data was decimated to 20 Hz using a 20th-order FIR filter to evaluate the 3 Hz features. Key times surrounding seizures were reviewed at 10 kHz. Video of the patient aligned to the electrophysiology with ~100 ms precision was part of the clinical record and was reviewed to acquire patient quotes during stimulation mapping. For quantification, 10 seconds of pre-seizure data were used, z-scored, and the power spectral density (PSD) was then estimated using Welch's method (pwelch in Matlab). The average band power within a specified band (3-4 Hz) was then computed by integrating the PSD estimate (bandpower( ) in Matlab). There was still an increase in band power in PMC during pre-seizure auras relative to non-seizure periods and to other regions when using the 1-4 Hz band, but there was baseline low frequency power in all regions that made the effect of the ~3 Hz oscillation smaller. The clinical stimulus pulse pattern used was 50 Hz biphasic stimulation for 1-2 s.

Supplementary Note 1: Clinical Interview with Epileptologist.

Seizure description.

PATIENT: "It would probably be better to just let you know right now that there is also a beta component to my spatial disorientation where like if you were to spin me around I would lose what is up, what is down . . . just throwing that out there."

EPILEPTOLOGIST: "If I spin you around . . . "

PATIENT: "If I was sitting in a chair that could spin and you were to spin that chair in any direction, I would lose my understanding of . . . "

EPILEPTOLOGIST: "Were you born like this?"

PATIENT: "No, I had a very slow seizure a few days ago and it was one the most interesting experiences of my life. It was like—kinda like this, imagine if you were just like stretching it, it was not more intense, but because I can think through my seizures, I was able to experience the whole seizure slowly . . . it was really cool"

EPILEPTOLOGIST: "Because you are also on medications as well, that could probably . . . so what happened?"

PATIENT: "So I, the first thing I noticed was that it felt like the whole world (again, I am going to use those 6 degrees of freedom I was talking to you about . . . so the three spatial dimensions and then beta x, beta y and beta z), I could feel them move and then the next thing I knew, I was feeling the emotion or feeling of where in this 3D space am I? And I went through the feeling of the process very slowly of refiguring that out, but it was like listening to another conversation in my brain."

EPILEPTOLOGIST: "Tell me more"

PATIENT: Laughs, "I really enjoyed it . . . um, it was kind of like, um, the experiencing, like you know, ok, there are . . . I am just going to describe it like a computer because that is the best way that I know how to describe it."

EPILEPTOLOGIST: "Yes, sure, sure"

PATIENT: "Imagine there are these two ICs speaking with each other, two components, right, but there is one data buff. Are you familiar with a data buff?"

EPILEPTOLOGIST: "I wish I were familiar, but no, consider me a complete idiot"

PATIENT: "Alright, what it does is that there is this one information highway (and what it does . . . ) and I want to speak with this component x, y and z. A and B are speaking, but they can only speak amongst this information highway that the CPU is always able to listen to. So I am listening to A and B speak with each other to try to figure out what the hell is going on and as a result, I am listening to this conversation, the CPU is trying to figure out . . . maybe I don't know what the "me" is, I don't know what that means necessarily, I personally don't believe in the idea of a soul, personally, but you know I was aware that I was listening to two parts of my brain speak to each other in a way that a third part of my brain, which I considered me, was able to listen. And what that felt like was this, it felt like a depersonalization, if you were to say . . . my friend asked me this recently, what would it feel like if someone else were to come into your head? That is exactly what it felt like . . . what I considered me shrank to this other part of me where the other parts of my brain that were talking, I stopped considering them me"

EPILEPTOLOGIST: "Interesting."

PATIENT: "So, that's why, for example, I took a blanket because I was interested in what was going on—I threw it over my body, just to see, because I knew that when I don't feel it, I don't consider it me and immediately my legs were no longer a part of me, in the way that that part of me was thinking, that part of my brain that I considering me was thinking so it was kind of like I was closed off, but I could hear the conversation—just like if you two were talking and you were saying "No we're upside down" and she was saying "No we're left side up", you know, I was listening to that and getting information that you two could not get so that's why I would do things like grab or throw something so that these two could say "oh look that just fell" and to try to convince them that what I am getting from here . . . it was really weird, but I thought you would find it interesting."

Supplementary Note 2

One characteristic of seizures is increased synchrony. While the ketamine-induced rhythm involved increased synchrony in neuronal firing, the initiation, spread, maintenance/termination, and behavior were distinguishable from typical seizures. Seizures display abrupt transitions in activity at onset and exhibit uncontrolled, variable duration; in contrast, the ketamine-induced oscillation emerged gradually over 2 minutes and decayed reliably and predictably over ~15 minutes. Moreover, while seizures spread from the focus to other areas and across layers [49], the ketamine-rhythm did not spread beyond layer 5 neurons in retrosplenial cortex-neither to other layers nor to nearby cortical regions; cells at the periphery of the retrosplenial cortex were not recruited later, and ketamine-induced activity did not spread laterally to visual cortex, and no rigidity, convulsive movements, absence-like states, or salivation/rearing/falling were observed in response to dissociative doses of ketamine.

REFERENCES

1. Ferezou, I. et aL. Spatiotemporal dynamics of cortical sensorimotor integration in behaving mice. *Neuron* 56, 907-23 (2007).
2. Mohajerani, M. H. et al. Spontaneous cortical activity alternates between motifs defined by regional axonal projections. *Nat. Neurosci.* 16, 1426 (2013).
3. Musall, S., Kaufman, M. T., Juavinett, A. L., Gluf, S. & Churchland, A. K. Single-trial neural dynamics are dominated by richly varied movements. *Nat. Neurosci.* 22, 1677-1686 (2019).
4. Kauvar, I. V. et al. Cortical Observation by Synchronous Multifocal Optical Sampling Reveals Widespread Population Encoding of Actions. *Neuron* 107, 351-367.e19 (2020).
5. Guo, Z. V et al. Flow of cortical activity underlying a tactile decision in mice. *Neuron* 81, 179-194 (2014).
6. Wekselblatt, J. B., Flister, E. D., Piscopo, D. M. & Niell, C. M. Large-scale imaging of cortical dynamics during sensory perception and behavior. *J. Neurophysiol.* 115, 2852-2866 (2016).
7. Ma, Y. et al. Resting-state hemodynamics are spatiotemporally coupled to synchronized and symmetric neural activity in excitatory neurons. *Proc. Natl. Acad. Sci. U.S.A* 113, E8463-E8471 (2016).
8. Allen, W. E. et al. Global Representations of Goal-Directed Behavior in Distinct Cell Types of Mouse Neocortex. *Neuron* 94, 891-907.e6 (2017).
9. Makino, H. et al. Transformation of Cortex-wide Emergent Properties during Motor Learning. *Neuron* 94, 880-890.e8 (2017).
10. Chen, T.-W., Li, N., Daie, K. & Svoboda, K. A Map of Anticipatory Activity in Mouse Motor Cortex. *Neuron* 94, 866-879.e4 (2017).
11. Xiao, D. et al. Mapping cortical mesoscopic networks of single spiking cortical or sub-cortical neurons. *Elife* 6, (2017).
12. Gilad, A., Gallero-Salas, Y., Groos, D. & Helmchen, F. Behavioral Strategy Determines Frontal or Posterior Location of Short-Term Memory in Neocortex. *Neuron* 99, 814-828.e7 (2018).
13. American Psychiatric Association. *Diagnostic and statistical manual of mental disorders* (5th ed.). (2013).
14. Krystal, J. H. et al. Subanesthetic Effects of the Noncompetitive NMDA Antagonist, Ketamine, in Humans: Psychotomimetic, Perceptual, Cognitive, and Neuroendocrine Responses. *Arch. Gen. Psychiatry* 51, 199-214 (1994).
15. Guo, Z. V et aL. Procedures for behavioral experiments in head-fixed mice. *PLoS One* 9, (2014).
16. Gil-Sanz, C. et aL. Lineage Tracing Using Cux2-Cre and Cux2-CreERT2 Mice. *Neuron* 86, 1091-1099 (2015).
17. Gerfen, C. R., Paletzki, R. & Heintz, N. GENSAT BAC cre-recombinase driver lines to study the functional organization of cerebral cortical and basal ganglia circuits. *Neuron* 80, 1368-83 (2013).
18. Allen, W. E. et aL. Thirst-associated preoptic neurons encode an aversive motivational drive. *Science* 357, 1149-1155 (2017).
19. DeNardo, L. A. et aL. Temporal evolution of cortical ensembles promoting remote memory retrieval. *Nat. Neurosci.* 22, 460-469 (2019).
20. Oh, S. W. et aL. A mesoscale connectome of the mouse brain. *Nature* 508, 207-214 (2014).
21. Hunnicutt, B. J. et aL. A comprehensive thalamocortical projection map at the mesoscopic level. *Nat. Neurosci.* 17, 1276-1285 (2014).
22. Phillips, J. W. et aL. A repeated molecular architecture across thalamic pathways. *Nat. Neurosci.* 22, 1925-1935 (2019).
23. McCormick, D. A. & Pape, H. C. Properties of a hyperpolarization-activated cation current and its role in rhythmic oscillation in thalamic relay neurones. *J. Physiol.* 431, 291-318 (1990).
24. Leresche, N., Lightowler, S., Soltesz, I., Jassik-Gerschenfeld, D. & Crunelli, V. Low-frequency oscillatory activities intrinsic to rat and cat thalamocortical cells. *J. Physiol.* (1991). doi:10.1113/jphysiol.1991.sp018744
25. Poulet, J. F. A., Fernandez, L. M. J., Crochet, S. & Petersen, C. C. H. Thalamic control of cortical states. *Nat. Neurosci.* 15, 370-372 (2012).
26. Fogerson, P. M. & Huguenard, J. R. Tapping the Brakes: Cellular and Synaptic Mechanisms that Regulate Thalamic Oscillations. *Neuron* (2016). doi:10.1016/j.neuron.2016.10.024
27. MacDonald, J. F., Miljkovic, Z. & Pennefather, P. Use-dependent block of excitatory amino acid currents in cultured neurons by ketamine. *J. Neurophysiol.* 58, 251-66 (1987).
28. Anis, N. A., Berry, S. C., Burton, N. R. & Lodge, D. The dissociative anaesthetics, ketamine and phencyclidine, selectively reduce excitation of central mammalian neurones by N-methyl-aspartate. *Br. J. Pharmacol.* 79, 565-75 (1983).
29. Ludwig, A., Zong, X., Jeglitsch, M., Hofmann, F. & Biel, M. A family of hyperpolarization-activated mammalian cation channels. *Nature* (1998). doi:10.1038/31255
30. Santoro, B. et al. Identification of a gene encoding a hyperpolarization-activated pacemaker channel of brain. *Cell* (1998). doi:10.1016/S0092-8674(00)81434-8
31. Vogt, B. A. & Paxinos, G. Cytoarchitecture of mouse and rat cingulate cortex with human homologies. *Brain Struct. Funct.* 219, 185-192 (2014).
32. Foster, B. L. & Parvizi, J. Direct cortical stimulation of human posteromedial cortex. *Neurology* 88, 685-691 (2017).
33. Moda-Sava, R. N. et al. Sustained rescue of prefrontal circuit dysfunction by antidepressant-induced spine formation. *Science* 364, (2019).
34. Hua, T. et al. General anesthetics activate a potent central pain-suppression circuit in the amygdala. *Nat. Neurosci.* (2020). doi:10.1038/s41593-020-0632-8
35. Yang, Y. et al. Ketamine blocks bursting in the lateral habenula to rapidly relieve depression. *Nature* 554, 317-322 (2018).
36. Tomitaka, M., Tomitaka, S., Rajdev, S. & Sharp, F. R. Fluoxetine prevents PCP- and MK801-induced HSP70 expression in injured limbic cortical neurons of rats. *Biol. Psychiatry* 47, 836-841 (2000).

37. Olney, J. W., Labruyere, J. & Price, M. T. Pathological changes induced in cerebrocortical neurons by phencyclidine and related drugs. *Science* (80-.). 244, 1360-1362 (1989).

38. Mason, M. F. et al. Wandering minds: the default network and stimulus-independent thought. *Science* (80-.). 315, 393-395 (2007).

39. Raichle, M. E. The Brain's Default Mode Network. *Annu. Rev. Neurosci.* 38, 433-447 (2015).

40. Kohrs, R. & Durieux, M. E. Ketamine: teaching an old drug new tricks. *Anesth. Analg.* 87, 1186-1193 (1998).

41. Green, S. M., Roback, M. G., Kennedy, R. M. & Krauss, B. Clinical Practice Guideline for Emergency Department Ketamine Dissociative Sedation: 2011 Update. *Ann. Emerg. Med.* 57, 449-461 (2011).

42. Schwenk, E. S. et al. Consensus Guidelines on the Use of Intravenous Ketamine Infusions for Acute Pain Management From the American Society of Regional Anesthesia and Pain Medicine, the American Academy of Pain Medicine, and the American Society of Anesthesiologists. *Reg. Anesth. Pain Med.* 43, 456 (2018).

43. Jun, J. J. et al. Fully integrated silicon probes for high-density recording of neural activity. *Nature* 551, 232-236 (2017).

44. Putzeys, J. et al. Neuropixels Data-Acquisition System: A Scalable Platform for Parallel Recording of 10 000+ Electrophysiological Signals. *IEEE Trans. Biomed. Circuits Syst.* 13, 1635-1644 (2019).

45. Stringer, C. et al. Spontaneous behaviors drive multidimensional, brainwide activity. *Science* 364, 255 (2019).

46. Allen, W. E. et al. Thirst regulates motivated behavior through modulation of brainwide neural population dynamics. *Science* 364, 253 (2019).

47. Zalocusky, K. A. et al. Nucleus accumbens D2R cells signal prior outcomes and control risky decision-making. *Nature* 531, 642-646 (2016).

48. Gunaydin, L. a. et al. Natural neural projection dynamics underlying social behavior. *Cell* 157, 1535-1551 (2014).

49. Wenzel, M., Hamm, J. P., Peterka, D. S. & Yuste, R. Acute focal seizures start as local synchronizations of neuronal ensembles. *J. Neurosci.* 3176-18 (2019). doi: 10.1523/JNEUROSCI.3176-18.2019

Example 2

Modulation of HCN Pacemaker Channels

The molecular studies of rodent retrosplenial cortex described in Example 1 revealed increased expression of the rhythm-generating channel hyperpolarization-activated cyclic nucleotide-gated potassium channel 1 (HCN1) (proteins that sit on the membranes of neurons and influence the activity of the cells), which has been shown to play important roles in oscillatory neural activity. We found that this gene was naturally expressed at very high levels in the retrosplenial cortex in mice, but no other cortical areas. When we removed these HCN1 pacemaker channels from the retrosplenial cortex using gene editing, the dissociative drug ketamine no longer induced the deep retrosplenial rhythm and did not fully elicit the dissociation-like behavioral effects. Thus, HCN pacemaker channels in the posteromedial cortex were shown to be required for the dissociative effects of traditional dissociative drugs, with thalamic nuclei likely playing an important functional role, and are molecular targets for modulation of associative/dissociative symptoms.

Channel activity of HCN pacemaker channels, including HCN1, HCN2, HCN3, and HCN4 can be modulated by clinically approved drugs such as gabapentin, lamotrigine, ivabradine, amiodarone, clonidine, loperamide). Intracellular HCN channel trafficking can be stimulated or suppressed via modulation of TRIP8b/Pex5.

Example 3

Management of Dissociation or Disorders of Association

Expression levels of rhythm-generating channels (e.g. HCN1) in the posteromedial cortex can be evaluated by immunohistochemical or other pathology assessment such as by biopsy or other labeling method, invasive or noninvasive, for clinical use in diagnosis or management of dissociation or disorders of association.

Example 4

Modulation of Posteromedial Cortical Activity

Posteromedial cortical activity can be stimulated or inhibited by administering modulators of NMDAR channels or with clinically approved drugs such as, but not limited to, lidocaine, bupivacaine, propofol, benzodiazepines, and barbiturates. Posteromedial cortical activity may be indirectly modulated as well, using, for example monoamine oxidase inhibitors. Dissociation can be elicited using ketamine, PCP or other dissociative drugs, either globally or targeted to specific brain regions such as the posteromedial cortex or anterior thalamic nuclei. Methods for modulation can include, but are not limited to, global (IV, IM, PO, peritoneal, etc.) and/or local (intracranial infusion, ultrasound uncaging) administration of such agents.

What is claimed is:

1. A method of screening a candidate agent to determine if the candidate agent induces or inhibits a dissociative state in a subject, the method comprising:
   a) administering the candidate agent to the subject; and
   b) detecting whether the candidate agent induces or inhibits rhythmic neural activity in the posteromedial cortex of the subject.

2. The method of claim 1, wherein said detecting the rhythmic neural activity in the posteromedial cortex of the subject comprises performing electrocorticography (ECoG), electroencephalography (EEG), stereoelectroencephalography (sEEG), magnetoencephalography (MEG), single photon emission computed tomography (SPECT), functional magnetic resonance imaging (fMRI), or positron emission tomography (PET).

3. The method of claim 1, further comprising administering a dissociative agent that induces rhythmic neural activity in the posteromedial cortex; and detecting whether the candidate agent inhibits the rhythmic neural activity induced by the dissociative agent.

4. The method of claim 3, wherein the dissociative agent is ketamine or phencyclidine.

* * * * *